Figure 1:
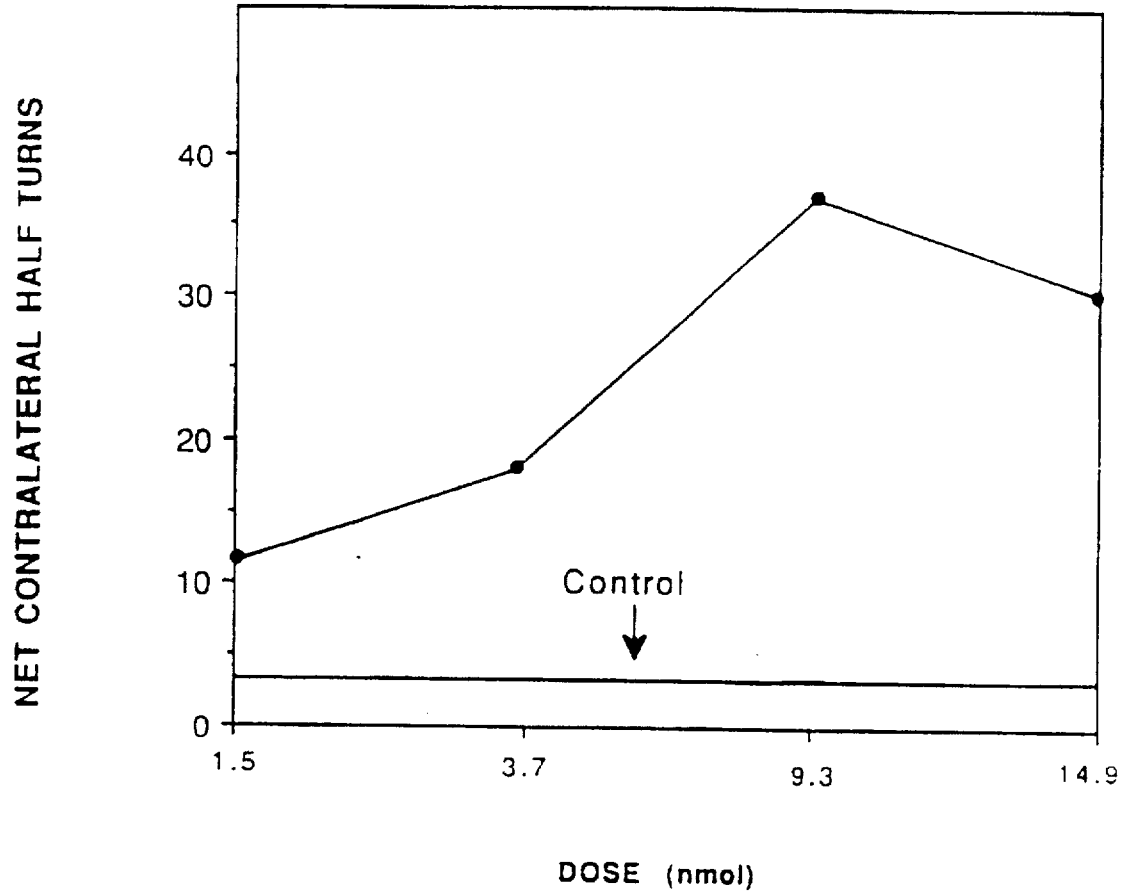

United States Patent [19]

de Costa et al.

[11] Patent Number: 5,739,158
[45] Date of Patent: Apr. 14, 1998

[54] NITROGEN-CONTAINING CYCLOHETERO CYCLOALKYLAMINOARYL DERIVATIVES FOR CNS DISORDERS

[75] Inventors: Brian R. de Costa, Gaithersburg; Kenner C. Rice, Bethesda, both of Md.; Nancy M. Gray, Buffalo Grove; Patricia C. Contreras, Evanston, both of Ill.; Arthur E. Jacobson, Potomac, Md.; Andrew Thurkauf, Banford, Conn.; Lilian A. Radesca, Brookeville, Md.; Wayne D. Bowen, East Providence; J. Michael Walker, Cranston, both of R.I.

[73] Assignee: The United States of America as represented by the Department of Health and Human Services, Washington, D.C.

[21] Appl. No.: 877,190

[22] PCT Filed: Jan. 31, 1991

[86] PCT No.: PCT/US91/00688

§ 371 Date: Jul. 1, 1992

§ 102(e) Date: Jul. 1, 1992

[87] PCT Pub. No.: WO91/12247

PCT Pub. Date: Aug. 22, 1991

Related U.S. Application Data

[63] Continuation-in-part of Ser. No. 473,008, Jan. 31, 1990, Pat. No. 5,130,330.

[51] Int. Cl.[6] .................. A61K 31/40; C07D 295/073; C07D 295/135
[52] U.S. Cl. .................................. 514/429; 548/578
[58] Field of Search ..................... 548/578; 514/429

[56] References Cited

U.S. PATENT DOCUMENTS

| | | | |
|---|---|---|---|
| 4,204,003 | 5/1980 | Szmuszkovicz | 560/27 X |
| 4,460,600 | 7/1984 | Kaplan et al. | 548/578 X |
| 4,463,013 | 7/1984 | Collins et al. | 548/407 X |
| 4,466,977 | 8/1984 | McMillan et al. | 548/578 X |
| 4,801,604 | 1/1989 | Vonvoigtlander et al. | 514/429 |
| 4,855,316 | 8/1989 | Horwell et al. | 514/429 X |
| 4,876,269 | 10/1989 | Penney et al. | 548/578 X |
| 4,891,382 | 1/1990 | Lancaster et al. | 514/429 |
| 5,130,330 | 7/1992 | de Costa et al. | 514/429 |

FOREIGN PATENT DOCUMENTS

| | | |
|---|---|---|
| 0372466 | 6/1990 | European Pat. Off. |

OTHER PUBLICATIONS

Brian R. de Costa et al; Journal of Medicinal Chemistry, vol. 33, No. 11, Nov. 1990; pp. 3100–3110.
S.M. Rothman and J. W. Olney, "Glutamate and the Pathophysiology of Hypoxia–Ischemic Brain Damage," *Annals of Neurology*, vol. 19, No. 2, pp. 105–111; (1986).
C. Carter et al, *J. Pharm. Exp. Ther.*, 247, (3), pp. 1222–1232; (1988).
A.F. Gilman et al, *The Pharmacological Basis of Therapeutics*, 7th Edn., p. 404, Macmillan; (1985).
C.G. Parsons et al, *Neuropharm.*, 25 (2); pp. 217–220; (1986).
W. Larson et al, *Brain Res.*, 482; pp. 333–339; (1989).
B.R. de Costa et al, *J. Med. Chem.*, 32(8); pp. 1996–2002; (1989).

*Primary Examiner*—Fiona T. Powers
*Attorney, Agent, or Firm*—Leydig, Voit & Mayer, Ltd.

[57] ABSTRACT

Certain nitrogen-containing cyclohetero cycloalkylaminoaryl compounds are described for treatment of CNS disorders such as cerebral ischemia, psychotic disorders, convulsions and parkinsonism. Compounds of particular interest are of the formula

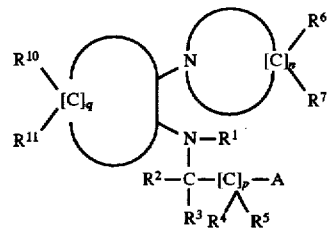

wherein $R^1$ is selected from hydrido, loweralkyl, cycloalkylalkyl of four to six carbon atoms and loweralkenylloweralkyl; wherein each of $R^2$ and $R^3$ is independently selected from hydrido and loweralkyl; wherein each of $R^4$ through $R^7$, $R^{10}$ and $R^{11}$ is independently selected from hydrido, hydroxy, loweralkyl, benzyl, phenoxy, benzyloxy and haloloweralkyl; wherein n is a number selected from four through six; wherein p is a number selected from zero through four; wherein q is a number selected from three through five; wherein A is selected from phenyl, naphthyl and thienyl; wherein any of the foregoing A groups can be further substituted with one or more substituents independently selected from hydrido, hydroxy, loweralkyl, loweralkoxy, halo, haloloweralkyl, amino, monoloweralkylamino and diloweralkylamino; or a pharmaceutically acceptable salt thereof.

15 Claims, 1 Drawing Sheet

NITROGEN-CONTAINING CYCLOHETERO CYCLOALKYLAMINOARYL DERIVATIVES FOR CNS DISORDERS

RELATED APPLICATION

This is a continuation-in-part of U.S. application Ser. No. 07/473,008 filed on Jan. 31, 1990, now U.S. Pat. No. 5,130,330, and a 371 of PCT/US91/00688 filed Jan. 31, 1991.

FIELD OF THE INVENTION

This invention is in the field of clinical neurology and relates specifically to a class of therapeutically useful compounds, compositions and methods for treatment of Central Nervous System (CNS) dysfunctions, neurotoxic damage, or neurodegenerative diseases. For example, these compounds are particularly useful for treating neurotoxic injury which follows periods of hypoxia, anoxia or ischemia associated with stroke, cardiac arrest or perinatal asphyxia. These compounds are also useful as antipsychotics and anticonvulsives.

BACKGROUND OF THE INVENTION

Unlike other tissues which can survive extended periods of hypoxia, brain tissue is particularly sensitive to deprivation of oxygen or energy. Permanent damage to neurons can occur during brief periods of hypoxia, anoxia or ischemia. Neurotoxic injury is known to be caused or accelerated by certain excitatory amino acids (EAA) found naturally in the central nervous system (CNS). Glutamate (Glu) is an endogenous amino acid which has been characterized as a fast excitatory transmitter in the mammalian brain. Glutamate is also known as a powerful neurotoxin capable of killing CNS neurons under certain pathological conditions which accompany stroke and cardiac arrest. Normal glutamate concentrations are maintained within brain tissue by energy-consuming transport systems. Under low energy conditions which occur during conditions of hypoglycemia, hypoxia or ischemia, cells can release glutamate. Under such low energy conditions the cell is not able to take glutamate back into the cell. Initial glutamate release stimulates further release of glutamate which results in an extracellular glutamate accumulation and a cascade of neurotoxic injury.

It has been shown that the sensitivity of central neurons to hypoxia and ischemia can be reduced by either blockage of synaptic transmission or by the specific antagonism of postsynaptic glutamate receptors [see S. M. Rothman and J. W. Olney, "Glutamate and the Pathophysiology of Hypoxia—Ischemic Brain Damage," *Annals of Neurology*, Vol. 19, No. 2 (1986)]. Glutamate is characterized as a broad spectrum agonist having activity at three neuronal excitatory amino acid receptor sites. These receptor sites are named after the amino acids which selectively excite them, namely: Kainate (KA), N-methyl-D-aspartate (NMDA or NMA) and quisqualate (QUIS).

Neurons which have EAA receptors on their dendritic or somal surfaces undergo acute excitotoxic degeneration when these receptors are excessively activated by glutamate. Thus, agents which selectively block or antagonize the action of glutamate at the EAA synaptic receptors of central neurons can prevent neurotoxic injury associated with hypoxia, anoxia, or ischemia caused by stroke, cardiac arrest or perinatal asphyxia.

It is known that compounds of various structures, such as aminophosphonovalerate derivatives and piperidine dicarboxylate derivatives, may act as competitive antagonists at the NMDA receptor. Certain piperidineethanol derivatives, such as ifenprodil and 1-(4-chlorophenyl)-2-[1-(4-fluorophenyl)piperidinyl]ethanol, which are known anti-ischemic agents, have been found to be non-competitive NMDA receptor antagonists [C. Carter et al, *J. Pharm Exp. Ther.*, 247 (3), 1222–1232 (1988)].

There are many classes of compounds known for treatment of psychotic disorders. For example, current therapeutic treatments for psychoses use compounds classifiable as phenothiazine-thioxanthenes, as phenylbutylpiperidines and also as certain alkaloids. An example of a phenylbutylpiperidine compound of current use in psychotic treatment therapy is haloperidol [A. F. Gilman et al, *The Pharmacological Basis of Theraputics*, 7th Edn., p. 404, MacMillan (1985)].

Certain nitrogen-containing cyclohetero cycloalkylaminoaryl compounds are known for pharmaceutical purposes. For example, U.S. Pat. No. 4,204,003 to Szmuszkovicz describes N-(2-aminocyclopentyl)-N-alkanoylanilides as antidepressant agents.

Certain aminocycloaliphatic benzamides have been described for various uses. For example, U.S. Pat. No. 4,463,013 to Collins et al describes aminocyclohexylbenzamides for use as diuretic agents. The compound (±)-trans-3,4-dichloro-N-methyl-N-[2-(1-pyrrolidinyl)cyclohexyl] benzene-acetamide has been evaluated for its selectivity as an amino acid antagonist [C. G. Parsons et al, *Neuropharm.*, 25(2), 217–220 (1986)]. This same compound has been evaluated for its neuroprotective activity against kainate-induced toxicity [W. Lason et al, *Brain Res.*, 482, 333–339 (1989)]. U.S. Pat. No. 4,801,604 to Vonvoightlander et al describes certain cis-N-(2-aminocycloaliphatic)benzamides as anticonvulsants including, specifically, the compound cis-3,4-dichloro-N-methyl-N-[2-(1-pyrrolidinyl) cyclohexyl]benzamide. These benzeneacetamide derivatives, such as trans-3,4-dichloro-N-methyl-N-[2-(1-pyrrolidinyl)cyclohexyl]-benzeneacetamide, have been described as a highly selective ligand for kappa opioid receptors. Such kappa opioid affinity is believed associated with blockade of convulsions and protection from cerebral ischemia [B. R. de Costa et al, *J. Med. Chem.*, 2(8), 1996–2002 (1989)].

DESCRIPTION OF THE INVENTION

Treatment of CNS disorders and diseases such as cerebral ischemia, psychotic disorders, convulsions and parkinsonism, as well as prevention of neurotoxic damage and neurodegenerative diseases, may be accomplished by administration of a therapeutically-effective amount of a compound of Formula I:

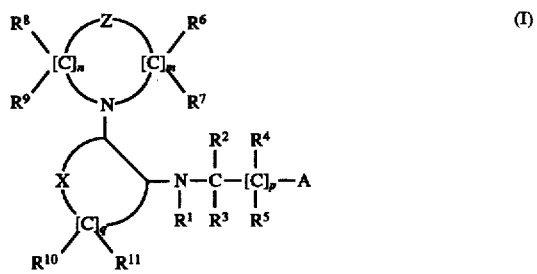

wherein $R^1$ is selected from hydrido, alkyl, cycloalkyl, hydroxyalkyl, haloalkyl, cycloalkylalkyl, alkoxyalkyl, aralkyl, aryl, alkenylalkyl, alkynylalkyl, carboxyalkyl, alkanoyl, alkylsulfinyl, alkylsulfonyl, arylsulfinyl and arylsulfonyl; wherein each of $R^2$ and $R^3$ is independently selected from hydrido, alkyl, cycloalkyl, hydroxyalkyl, haloalkyl, cycloalkylalkyl, alkoxyalkyl, aralkyl, aryl, alkenyl, alkynyl, alkenylalkyl, alkynylalkyl, carboxyalkyl, alkanoyl, alkoxycarbonyl, carboxy, cyanoalkyl, alkylsulfinyl, alkylsulfonyl, arylsulfinyl and arylsulfonyl; wherein $R^2$ and $R^3$ may be taken together to form a saturated or partially unsaturated carbocyclic group having three to eight ring carbons; wherein each of $R^4$ through $R^{11}$ is independently selected from hydrido, hydroxy, alkyl, cycloalkyl, cycloalkylalkyl, aralkyl, aryl, alkoxy, aryloxy, aralkoxy, alkoxyalkyl, haloalkyl, hydroxyalkyl, cyano, amino, monoalkylamino, dialkylamino, carboxy, carboxyalkyl, alkanoyl, alkenyl and alkynyl; wherein $R^4$ and $R^5$ may be taken; together to form oxo or to form a saturated or partially unsaturated carbocyclic group having three to eight ring carbons; wherein $R^6$ and $R^7$ may be taken together to form oxo; wherein $R^8$ and $R^9$ may be taken together to form oxo; wherein $R^{10}$ and $R^{11}$ may be taken together to form oxo; wherein each of n and m is a number selected from one through four; wherein each of p and q is a number selected from zero through five; wherein each of X and Z is independently selected from

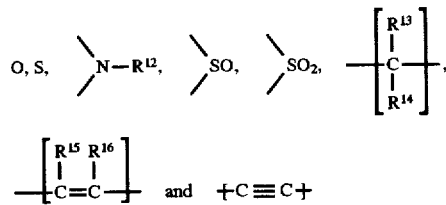

wherein $R^{12}$ may be selected from hydrido, alkyl, cycloalkyl, cycloalkylalkyl, aryl, aralkyl, heteroaryl, alkoxyalkyl, hydroxyalkyl, alkanoyl, aralkanoyl, aroyl, aminoalkyl, monoalkylaminoalkyl and dialkylaminoalkyl; wherein each of $R^{13}$ through $R^{16}$ is independently selected from hydrido, hydroxy, alkyl, cycloalkyl, cycloalkylalkyl, aralkyl, aryl, alkoxy, aralkoxy, aryloxy, alkoxyalkyl, haloalkyl, hydroxyalkyl, halo, cyano, amino, monoalkylamino, dialkylamino, carboxy, carboxyalkyl and alkanoyl; wherein A is selected from aryl, heteroaryl, aryloxy, heteroaryloxy, aralkoxy, heteroaralkoxy, arylamino, heteroarylamino, aralkylamino, heteroaralkylamino, arylthio, heteroarylthio, aralkylthio and heteroaralkylthio; wherein any of the foregoing A groups can be further substituted with one or more substituents independently selected from hydrido, hydroxy, alkyl, cycloalkyl, cycloalkylalkyl, aralkyl, aryl, alkoxy, aryloxy, aralkoxy, alkoxyalkyl, halo, haloalkyl, hydroxyalkyl, cyano, amino, monoalkylamino, dialkylamino, carboxy, carboxyalkyl, alkanoyl, alkenyl and alkynyl; or a pharmaceutically-acceptable salt thereof.

The family of compounds within Formula I is novel with the proviso that each of the compounds embraced by Formula I is a cis isomer with respect to the two nitrogen atoms of Formula I; or a pharmaceutically acceptable salt thereof.

A preferred family of compounds of Formula I consists of those compounds wherein $R^1$ is selected from hydrido, alkyl, cycloalkyl, hydroxyalkyl, haloalkyl, cycloalkylalkyl, alkoxyalkyl, aralkyl, aryl, alkenylalkyl, alkynylalkyl and carboxyalkyl; wherein each of $R^2$ and $R^3$ is independently selected from hydrido, alkyl, cycloalkyl, hydroxyalkyl, haloalkyl, cycloalkylalkyl, alkoxyalkyl, aralkyl, aryl, alkenyl, alkynyl, alkenylalkyl, alkynylalkyl, carboxyalkyl, alkanoyl, alkoxycarbonyl, carboxy and cyanoalkyl; wherein $R^2$ and $R^3$ may be taken together to form a saturated or partially unsaturated carbocyclic group having three to eight ring carbons; wherein each of $R^4$ through $R^{11}$ is independently selected from hydrido, hydroxy, alkyl, cycloalkyl, cycloalkylalkyl, aralkyl, aryl, alkoxy, aryloxy, aralkoxy, alkoxyalkyl, haloalkyl, hydroxyalkyl, cyano, amino, monoalkylamino, dialkylamino, carboxy, carboxyalkyl, alkanoyl, alkenyl and alkynyl; wherein $R^4$ and $R^5$ may be taken together to form oxo or to form a saturated or partially unsaturated carbocyclic group having three to eight ring carbons; wherein each of n and m is a number selected from one through four; wherein each of p and q is a number selected from zero through five; wherein X is selected from

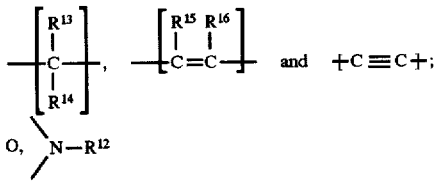

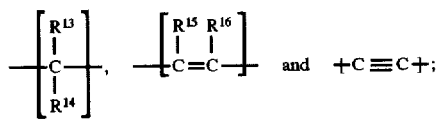

wherein $R^{12}$ may be selected from hydrido, alkyl, cycloalkyl, cycloalkylalkyl, aryl, aralkyl, heteroaryl, alkoxyalkyl, hydroxyalkyl, alkanoyl, aralkanoyl, aroyl, aminoalkyl, monoalkylaminoalkyl and dialkylaminoalkyl; wherein each of $R^{13}$ through $R^{16}$ is independently selected from hydrido, hydroxy, alkyl, cycloalkyl, cycloalkylalkyl, aralkyl, aryl, alkoxy, aralkoxy, aryloxy, alkoxyalkyl, haloalkyl, hydroxyalkyl, halo, cyano, amino, monoalkylamino, dialkylamino, carboxy, carboxyalkyl and alkanoyl; wherein A is selected from aryl, heteroaryl, aryloxy, heteroaryloxy, aralkoxy, heteroaralkoxy, arylamino, heteroarylamino, aralkylamino, heteroaralkylamino, arylthio, heteroarylthio, aralkylthio and heteroaralkylthio; wherein any of the foregoing A groups can be further substituted with one or more substituents independently selected from hydrido, hydroxy, alkyl, cycloalkyl, cycloalkylalkyl, aralkyl, aryl, alkoxy, aryloxy, aralkoxy, alkoxyalkyl, halo, haloalkyl, hydroxyalkyl, cyano, amino, monoalkylamino, dialkylamino, carboxy, carboxyalkyl, alkanoyl, alkenyl and alkynyl; or a pharmaceutically acceptable salt thereof.

A more preferred family of compounds within Formula I consists of those compounds wherein $R^1$ is selected from hydrido, loweralkyl, cycloalkyl of three to about eight carbon atoms, hydroxyloweralkyl, haloloweralkyl, cycloalkylalkyl of four to about eight carbon atoms, loweralkoxyloweralkyl, phenylloweralkyl, phenyl, loweralkenylloweralkyl, loweralkynylloweralkyl and carboxyloweralkyl; wherein each of $R^2$ and $R^3$ is independently selected from hydrido, loweralkyl, cycloalkyl of three to about eight carbon atoms, hydroxyloweralkyl, haloloweralkyl, cycloalkylalkyl of four to about eight carbon atoms, loweralkoxyloweralkyl, phenylloweralkyl, phenyl, loweralkenyl, loweralkynyl, loweralkenylloweralkyl, loweralkynylloweralkyl, carboxyloweralkyl, loweralkanoyl, loweralkoxycarbonyl, carboxy and cyanoloweralkyl; wherein $R^2$ and $R^3$ may be taken together to form a saturated or partially unsaturated carbocyclic group having three to eight ring carbons; wherein each of $R^4$ through $R^{11}$ is independently selected from hydrido, hydroxy, loweralkyl, cycloalkyl of three to about eight carbon atoms, cycloalkylalkyl of four to about eight carbon atoms, phenylloweralkyl, phenyl, loweralkoxy, phenoxy, phenylloweralkoxy, loweralkoxyloweralkyl, haloloweralkyl, hydroxyloweralkyl, cyano, amino, monoloweralkylamino, diloweralkylamino, carboxy, carboxyloweralkyl, loweralkanol, loweralkenyl and loweralkynyl; wherein $R^4$ and $R^5$ may be taken together to form oxo or to form a saturated or partially unsaturated carbocyclic group having three to eight ring carbons; wherein each of n and m is a number selected from one through four; wherein each of p and q is a number selected from zero through five; wherein X is selected from

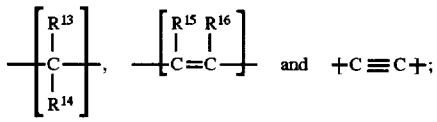

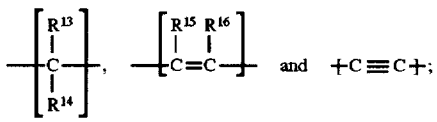

wherein $R^{12}$ may be selected from hydrido, loweralkyl, cycloalkyl of three to about eight carbon atoms, cycloalkylalkyl of four to about eight carbon atoms, phenyl, phenylloweralkyl, heteroaryl, loweralkoxyloweralkyl, hydroxyloweralkyl, loweralkanoyl, phenylalkanoyl, benzoyl, aminoloweralkyl, monoloweralkylaminolower-alkyl and diloweralkylaminoloweralkyl; wherein each of $R^{13}$ through $R^{16}$ is independently selected from hydrido, hydroxy, loweralkyl, cycloalkyl of three to about eight carbon atoms, cycloalkylalkyl of four to about eight carbon atoms, phenyloweralkyl, phenyl, loweralkoxy, phenylloweralkoxy, phenoxy, loweralkoxyloweralkyl, haloloweralkyl, hydroxyloweralkyl, halo, cyano, amino, monoloweralkylamino, diloweralkylamino, carboxy, carboxyloweralkyl and loweralkanoyl; wherein A is selected from phenyl, naphthyl, heteroaryl, phenoxy, naphthyloxy, heteroaryloxy, phenylloweralkoxy, naphthylloweralkoxy, heteroarylloweralkoxy, phenylamino, naphthylamino, heteroarylamino, phenylloweralkylamino, naphthylloweralkylamino, heteroaralkylamino, phenylthio, naphthylthio, heteroarylthio, phenylloweralkylthio and heteroarylloweralkylthio; wherein any of the foregoing A groups can be further substituted with one or more substituents independently selected from hydrido, hydroxy, loweralkyl, cycloalkyl of three to about eight carbon atoms, cycloalkylalkyl of four to about eight carbon atoms, phenylloweralkyl, phenyl, loweralkoxy, phenoxy, phenyloweralkoxy, loweralkoxyloweralkyl, halo, haloloweralkyl, hydroxyloweralkyl, cyano, amino, monoloweralkylamino, diloweralkylamino, carboxy, carboxyloweralkyl, loweralkanoyl, loweralkenyl and loweralkynyl; or a pharmaceutically acceptable salt thereof.

A more highly preferred family of compounds of Formula I consists of those compounds wherein $R^1$ is selected from hydrido, loweralkyl, cycloalkyl of three to about eight carbon atoms, cycloalkylalkyl of four to about eight carbon atoms, benzyl, phenyl, loweralkenylloweralkyl and loweralkynylloweralkyl; wherein each of $R^2$ and $R^3$ is independently selected from hydrido, loweralkyl, cycloalkyl of three to about eight carbon atoms, cycloalkylalkyl of four to about eight carbon atoms, benzyl, phenyl, loweralkenyl, loweralkynyl, loweralkenylloweralkyl, loweralkynylloweralkyl, loweralkanoyl and loweralkoxy-carbonyl; wherein $R^2$ and $R^3$ may be taken together to form a saturated or partially unsaturated carbocyclic group having three to eight ring carbons; wherein each of $R^4$ through $R^{11}$ is independently selected from hydrido, hydroxy, loweralkyl, cycloalkyl of three to about eight carbon atoms, cycloalkylalkyl of four to about eight carbon atoms, benzyl, phenyl, loweralkoxy, phenoxy, benzyloxy, loweralkoxyloweralkyl, haloloweralkyl, hydroxyloweralkyl, loweralkanoyl, loweralkenyl and loweralkynyl; wherein $R^4$ and $R^5$ may be taken together to form oxo or to form a saturated or partially unsaturated carbocyclic group having three to eight ring carbons; wherein each of n and m is a number selected from one through four; wherein each of p and q is a number selected from zero through five; wherein X is selected from

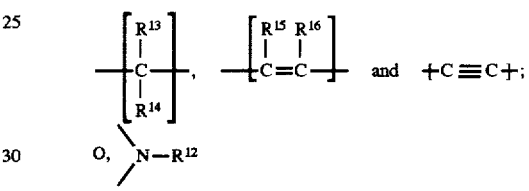

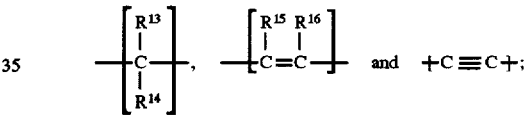

wherein $R^{12}$ may be selected from hydrido, loweralkyl, cycloalkyl of three to about eight carbon atoms, cycloalkylalkyl of four to about eight carbon atoms, phenyl, benzyl, loweralkoxyloweralkyl and hydroxyloweralkyl; wherein each of $R^{13}$ through $R^{16}$ is independently selected from hydrido, hydroxy, loweralkyl, cycloalkyl of three to about eight carbon atoms, cycloalkylalkyl of four to about eight carbon atoms, benzyl, phenyl, loweralkoxy, benzyloxy, phenoxy, loweralkoxyloweralkyl, haloloweralkyl, hydroxyloweralkyl and halo; wherein A :is selected from phenyl, naphthyl, thienyl, phenoxy, benzyloxy, naphthyloxy, thiophenoxy, phenylamino, benzylamino, naphthylamino, phenylthio, benzylthio and naphthylthio; wherein any of the foregoing A groups can be further substituted with one or more substituents independently selected from hydrido, hydroxy, loweralkyl, cycloalkyl of three to about eight carbon atoms, cycloalkylalkyl of four to about eight carbon atoms, loweralkoxy, loweralkoxyloweralkyl, halo, haloloweralkyl, hydroxyloweralkyl, amino, monoloweralkylamino, diloweralkylamino, loweralkanoyl, loweralkenyl and loweralkynyl; or a pharmaceutically acceptable salt thereof.

A family of compounds of particular interest within Formula I are compounds embraced by Formula II:

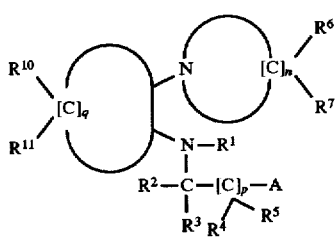

(II)

wherein R¹ is selected from hydrido, loweralkyl, cycloalkylalkyl of four to six carbon atoms and loweralkenylloweralkyl; wherein each of R² and R³ is independently selected from hydrido and loweralkyl; wherein each of R⁴ through R⁷, R¹⁰ and R¹¹ is independently selected from hydrido, hydroxy, loweralkyl, benzyl, phenoxy, benzyloxy and haloloweralkyl; wherein n is a number selected from four through six; wherein p is a number selected from zero through four; wherein q is a number selected from three through five; wherein A is selected from phenyl, naphthyl and thienyl; wherein any of the foregoing A groups can be further substituted with one or more substituents independently selected from hydrido, hydroxy, loweralkyl, loweralkoxy, halo, haloloweralkyl, amino, monoloweralkylamino and diloweralkylamino; or a pharmaceutically acceptable salt thereof.

A more preferred family of compounds within Formula II consists of compounds wherein R¹ is selected from hydrido, methyl, ethyl, propyl, cyclopropylmethyl, allyl and dimethylallyl; wherein each of R² and R³ is independently selected from hydrido, methyl, ethyl and propyl; wherein each of R⁴ through R⁷, R¹⁰ and R¹¹ is independently selected from hydrido, hydroxy, methyl, ethyl, propyl, benzyl, phenoxy, benzyloxy and haloloweralkyl; wherein n is a number selected from four or five; wherein p is a number selected from zero through two; wherein q is a number selected from three or four; wherein A is phenyl or naphthyl; wherein any of the foregoing A groups can be further substituted with one or more substituents independently selected from hydroxy, methyl, ethyl, propyl, methoxy, ethoxy, methylenedioxy, halo, trifluoromethyl, amino, methylamino and dimethylamine; or a pharmaceutically acceptable salt thereof.

Of highest interest are the following specific compounds:

(±)-cis-N-[2-(3,4-dichlorophenyl)ethyl]-2-(1-pyrrolidinyl)cyclohexylamine;
1S,2R-(+)-cis-N-[2-(3,4-dichlorophenyl)ethyl]-2-(1-pyrrolidinyl)cyclohexylamine;
1R,2S-(−)-cis-N-[2-(3,4-dichlorophenyl)ethyl]-2-(1-pyrrolidinyl)cyclohexylamine;
(±)-cis-N-[2-(3,4-dichlorophenyl)ethyl]-N-methyl-2-(1-pyrrolidinyl)cyclohexylamine;
1S,2R-(−)-cis-N-[2-(3,4-dichlorophenyl)ethyl]-N-methyl-2-(1-pyrrolidinyl)cyclohexylamine;
1R,2S-(+)-cis-N-[2-(3,4-dichlorophenyl)ethyl]-N-methyl-2-(1-pyrrolidinyl)cyclohexylamine;
(±)-cis-N-methyl-N-(2-phenylethyl)-2-(1-pyrrolidinyl)cyclohexylamine;
(±)-cis-N-methyl-N-[2-(β-naphthyl)ethyl]-2-(1-pyrrolidinyl)cyclohexylamine;
1S,2R-(−)-cis-N-methyl-N-[2-(3,4-methylenedioxyphenyl)ethyl]-2-(1-pyrrolidinyl)cyclohexylamine;
1R,2S-(+)-cis-N-methyl-N-[2-(3,4-methylenedioxyphenyl)ethyl]-2-(1-pyrrolidinyl)cyclohexylamine;
1R,2S-(−)-cis-N-[2-(3,4-dichlorophenyl)ethyl]-N-ethyl-2-1-pyrrolidinyl)cyclohexylamine;
1R,2S-(−)-cis-N-cyclopropylmethyl-N-[2-(3,4-dichlorophenyl)ethyl]-2-(1-pyrrolidinyl)cyclohexylamine;
1R,2S-(−)-cis-N-[2-(3,4-dichlorophenyl)ethyl]-N-(1-propyl)-2-(1-pyrrolidinyl)cyclohexylamine;
1S,2R-(+)-cis-N-[2-(3,4-dichlorophenyl)ethyl]-2-(1-pyrrolidinyl)cyclohexylamine;
1S,2R-(−)-cis-N-[2-(3,4-dichlorophenyl)ethyl]-N-ethyl-2-(1-pyrrolidinyl)cyclohexylamine;
1S,2R-(−)-cis-N-[2-(3,4-dichlorophenyl)ethyl]-N-cyclopropylmethyl-2-(1-pyrrolidinyl)cyclohexylamine;
1S,2R-(−)-cis-N-[2-(3,4-dichlorophenyl)ethyl]-N-(1-propyl)-2-(1-pyrrolidinyl)cyclohexylamine; and
(±)-cis-N-[2-(3,4-dichlorophenyl)methyl]-N-methyl-2-(1-pyrrolidinyl)cyclohexylamine.

The term "hydrido" denotes a single hydrogen atom (H). This hydrido group may be attached, for example, to an oxygen atom to form a hydroxyl group; or as another example, two hydrido groups may be attached to a carbon atom to form a divalent —CH₂— group, that is, a "methylene" group; or as another example, one hydrido group may be attached to a carbon atom to form a trivalent —CH< group. Where the term "alkyl" is used, either alone or within other terms such as "haloalkyl" and "hydroxyalkyl", the term "alkyl" embraces linear or branched radicals having one to about twenty carbon atoms or, preferably, one to about ten carbon atoms. More preferred alkyl radicals are "lower alkyl" radicals having one to about five carbon atoms. The term "cycloalkyl" embraces cyclic radicals having three to about six carbon atoms, such as cyclopropyl and cyclobutyl. The term "haloalkyl" embraces radicals wherein any one or more of the alkyl carbon atoms is substituted with one or more halo groups, preferable selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. A dihaloalkyl group, for example, may have two bromo atoms, such as a dibromomethyl group, or two chloro atoms, such as a dichloromethyl group, or one bromo atom and one chloro atom, such as a bromochloromethyl group. An example of a polyhaloalkyl is a trifluoromethyl group. The terms "alkylol" and "hydroxyalkyl" embrace linear or branched alkyl groups having one to about ten carbon atoms any one of which may be substituted with one or more hydroxyl groups. The term "alkenyl" embraces linear or branched radicals having two to about twenty carbon atoms, preferable two to about ten carbon atoms, and containing, least one carbon-carbon triple bond. The terms "cycloalkenyl" and "cycloalkynyl" embrace cyclic radical having three to about ten ring carbon atoms including, respectively, one or more double or triple bonds involving adjacent ring carbons. The terms "alkoxy" and "alkoxyal" embrace linear or branched oxy-containing radicals each having alkyl portions of one to about ten carbon atoms, such as methoxy group. The "alkoxy" or "alkoxyalkyl" radicals may be further substituted with one or more halo atoms, such as fluoro, chloro or bromo, to provide haloalkoxy or haloalkoxyalkyl groups. The term "heteroaryl" embraces aromatic ring systems containing one or two hetero atoms selected from oxygen, nitrogen and sulfur in a ring system having five or six ring members, examples of which are thienyl, furanyl, pyridinyl, thiazolyl, pyrimidyl and isoxazolyl. The term "alkylene chain" describes a chain of two to six methylene (—CH₂—) groups which may form a cyclic structure with or without a hetero atom in the cyclic structure.

Specific examples of alkyl groups are methyl, ethyl, n-propyl, isopropyl, n-butyl, sec-butyl, iso-butyl, tert-butyl, n-pentyl, iso-pentyl, methyl-butyl, dimethylbutyl and neopentyl. Typical alkenyl and alkynyl groups may have one unsaturated bond, such as an allyl group, or may have a plurality of unsaturated bonds, with such plurality of bonds either adjacent, such as allene-type structures, or in conjugation, or separated by several saturated carbons.

Included within the family of compounds of Formulas I–II are the tautomeric forms of the described compounds, isomeric forms including diastereoisomers, and the pharmaceutically-acceptable salts thereof. The term "pharmaceutically-acceptable salts" embraces salts commonly used to form alkali metal salts and to form addition salts of free acids or free bases. Since the compounds of Formulas I–II contain basic nitrogen atoms, such salts are typically acid addition salts. The phrase "pharmaceutically-acceptable salts" is not intended to embrace quaternary ammonium salts. The nature of the salt is not critical, provided that it is pharmaceutically acceptable, and acids which may be employed to form salts are, of course, well known to those skilled in this art. Examples of acids which may be employed to form pharmaceutically acceptable acid addition salts include such inorganic acids as hydrochloric acid, sulfuric acid and phosphoric acid, and such organic acids as maleic acid, succinic acid and citric acid. Other pharmaceutically acceptable salts include salts with alkali metals or alkaline earth metals, such as sodium, potassium, calcium and magnesium, or with organic bases, such as dicyclohexylamine. All of these salts may be prepared by conventional means by reacting, for example, the appropriate acid or base with the corresponding compound of Formulas I–II.

GENERAL SYNTHETIC PROCEDURES

Compounds of Formulas I and II may be prepared in accordance with the following generic procedures, within which specific schemes are shown for Formula II type compounds.

Step 1

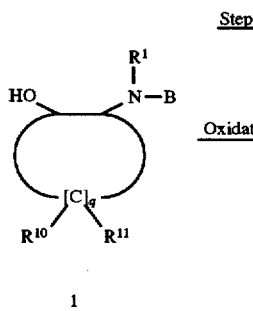

wherein $R^1$, $R^{10}$, $R^{11}$, and q are as defined previously; and wherein B represents a protecting group such as acetyl, benzoyl, t-butyloxy-carbonyl or benzyloxycarbonyl.

A process for preparing the compounds of the invention starts with protected hydroxyeines of general structure 1 where $R^1$, $R^{10}$, $R^{11}$, and q have the value assigned previously; and where B represents a protecting group such as acetyl, benzoyl or t.-butyloxycarbonyl. The alcohol is oxidized to the ketone 2 employing oxidizing agents such as pyridinium chlorochromate, chromium trioxide, potassium dichromate, or other oxidizing agents familiar to those skilled in the art. This oxidation can be achieved in either aqueous or organic solvents, depending on the oxidizing agent of choice, and at temperatures ranging from –60° to reflux of the reaction mixture.

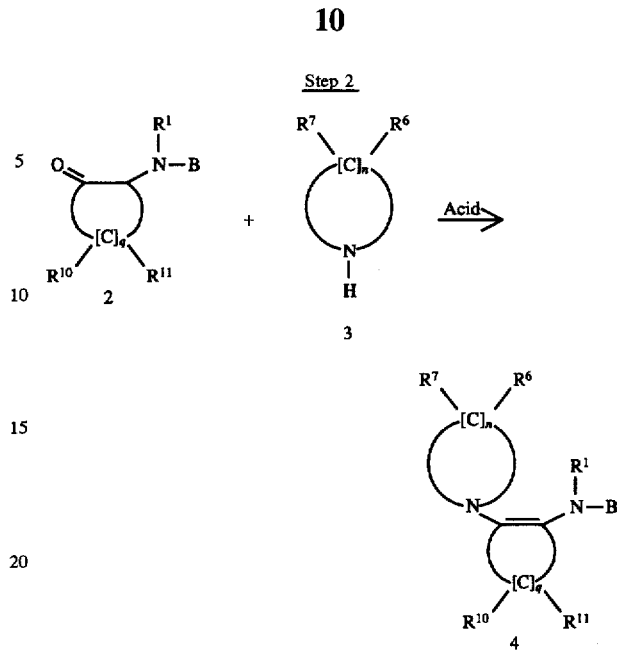

wherein B, $R^1$, $R^6$, $R^7$, $R^{10}$, $R^{11}$, n, and q are as defined previously.

In the second step of the process, ketones of general structure 2 are converted to enamines of general structure 4 by mixing 2 with amines of general structure 3 where B, $R^1$, $R^6$, $R^7$, $R^{10}$, $R^{11}$, n, and q are as defined previously. The compounds can be combined neat or in a variety of solvents such as toluene, xylene, or chloroform and with an acid such as p-toluenesulfonic acid, acetic acid, or trifluoroacetic acid. The temperature of the reaction can vary from room temperature to reflux of the reaction mixture.

Step 3

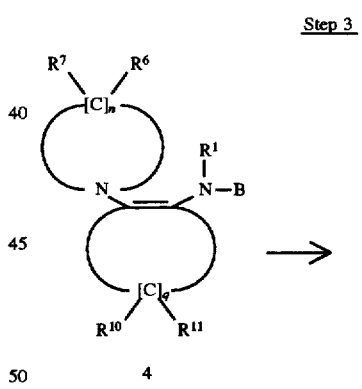

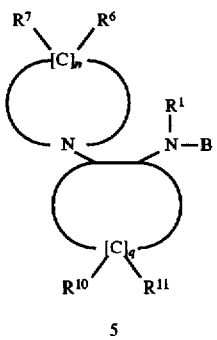

wherein B, $R^1$, $R^6$, $R^7$, $R^{10}$, $R^{11}$, n, and q are as defined previously.

In the third step of the process, enamines of general structure 4 are reduced to amines of general structure 5 by employing reducing agents such as lithium aluminum hydride, sodium borohydride, sodium cyanoborohydride, catalylic hydrogenation, or other reducing agents familiar to those skilled in the art. This reduction can be accomplished in either protic or aprotic solvents, depending on the reducing agent of choice, and at temperatures ranging from room temperature to reflux of the reaction mixture.

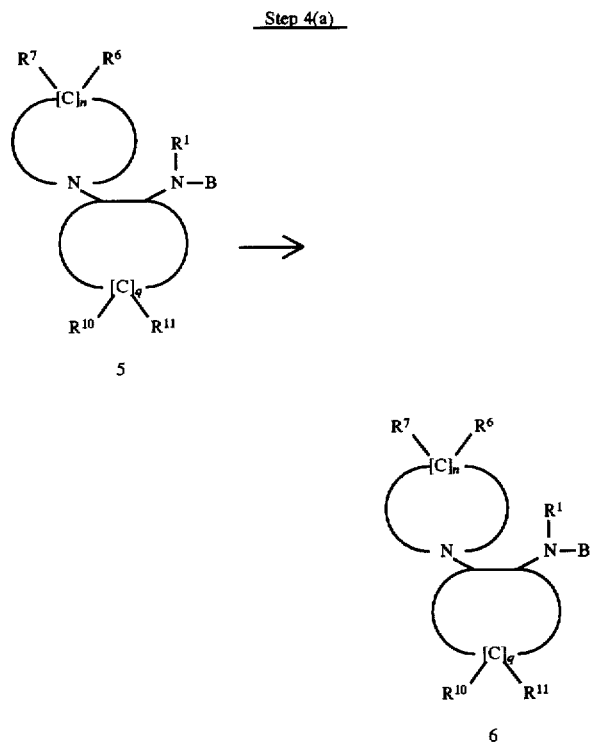

wherein B, $R^1$, $R^6$, $R^7$, $R^{10}$, $R^{11}$, n, and q are as defined previously.

In the fourth step of the process, amines of general structure 5 are converted to amines of general structure 6 by removal of the blocking group B. The conversion is best achieved by mixing 5 with a base such as sodium hydroxide, potassium hydroxide or other bases familiar to those skilled in the art. The reagents are combined in a protic solvent such as water, ethylene glycol, or methanol. The temperature of the reaction can vary from room temperature to reflux of the reaction mixture.

Step 4(b)

Alternately, amines of general structure 6 can be prepared from amines of general structure 5 by removal of the blocking group B by mixing 5 with an acid such as hydrochloric acid, sulfuric acid, trifluoroacetic acid or other acids familiar to those skilled in the art. The reagents are combined in a protic solvent such as water, ethylene glycol, or methanol. The temperature of the reaction can vary from room temperature to reflux of the reaction mixture.

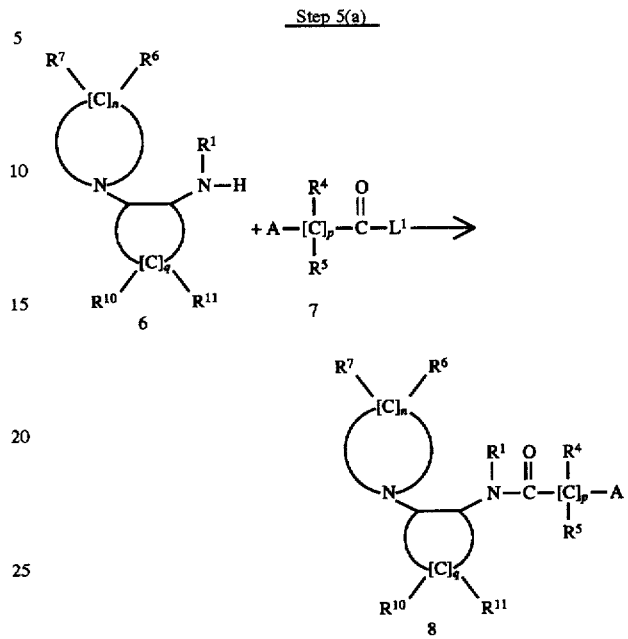

wherein A, $R^1$, $R^4$ through $R^7$, $R^{10}$, $R^{11}$, n, p, and q are as defined previously; and wherein $L^1$ is a good leaving group such as chloro, bromo, acyloxy, or hydroxy.

In the fifth step of the process, amines of general structure 6 are converted to amides of general structure 8 where A, $R^4$, and $R^5$ have the value assigned previously and $L^1$ is a good leaving group such as chloro, bromo, acyloxy, or hydroxy. The conversion can be best achieved by mixing the reagents neat or in an aprotic solvent such as tetrahydrofuran, methylene chloride, or ether. The reaction can be run in the absence or presence of an activating agent such as dicyclohexylcarbodiimide or phosphorus oxychloride, depending on the leaving group of choice. The temperature of the reaction can vary from 0° to reflux of the reaction mixture.

Step 6(a)

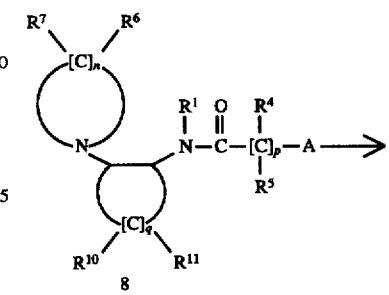

-continued
Step 6(a)

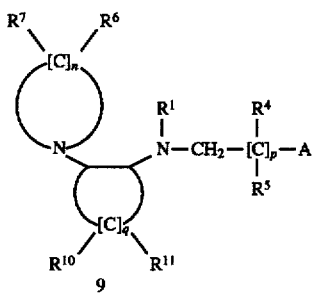

wherein A, $R^1$, $R^4$ through $R^7$, $R^{10}$, $R^{11}$, n, p, and q are as defined previously.

In the sixth step of the process, amides of general structure 8 are converted to amines of general structure 9 by employing reducing agents such as lithium aluminum hydride, sodium borohydride, sodium cyanoborohydride, or other reducing agents familiar to those skilled in the art. This reduction can be accomplished in either protic or aprotic solvents, depending on the reducing agent of choice, and at temperatures ranging from room temperature to reflux of the reaction mixture.

Step 5(b) [Alternate to Steps 5(a) and 5(b)]

Alternately, amines of general structure 11 can be prepared according to the following generic procedure.

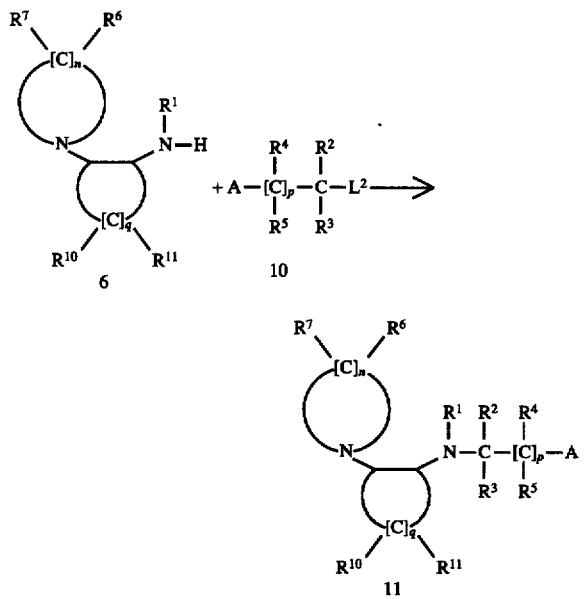

wherein A, $R^1$ through $R^7$, $R^{10}$, $R^{11}$, n, p, and q are as defined previously; and wherein $L^2$ is a good leaving group such as halogen, tosylate, mesylate, brosylate or OH.

Amines of general structure 11 can be alternately prepared by combining amines of general structure 6 with compounds of general structure 10 where A, $R^1$ through $R^7$, $R^{10}$, $R^{11}$, n, p, and q have the values assigned previously and where $L^2$ is a good leaving group such as halogen, tosylate, mesylate, brosylate or OH. The compounds can be combined in a variety of solvents such as toluene, xylenes, dimethylformamide, hexamethylphosphoramide, or ethanol. The temperature of the reaction can vary from room temperature to reflux of the reaction mixture.

The following Examples 1 to 6 are detailed descriptions of the methods of preparation of compounds of Formula I. These detailed preparations fall within the scope of, and serve to exemplify, the above described Generic Procedures which form part of the invention. These Examples 1 to 6 are presented for illustrative purposes only and are not intended as a restriction on the scope of the invention. All parts are by weight unless otherwise indicated. Most of the commercially available starting materials were obtained from Aldrich Chemical Company, Milwaukee, Wis. Abbreviated terms used in Examples 1 to 6 are explained below:

| MeOH | = | methanol |
|---|---|---|
| EtOH | = | ethanol |
| DMSO | = | dimethylsulfoxide |
| EtOAc | = | ethyl acetate |
| TLC | = | thin layer chromatography |
| $Et_2O$ | = | ethyl ether |
| $Ac_2O$ | = | acetic anhydride |
| $Et_3N$ | = | triethylamine |
| THF | = | tetrahydrofuran |

EXAMPLE I

Step (a): Preparation of (±)-trans-2-benzamidocyclohexanol (±)-trans-2-Aminocyclohexanol (241 gm) was combined with chloroform (2000 ml), water (2000 ml) and sodium bicarbonate (352 gm) and stirred. Benzoyl chloride (352 gm) was added dropwise to the stirred solution and stirring was continued for 1 hr. The product was filtered and washed with water. The white solid was dried at 80° C. to provide the product (mp 172°–173° C.).

Step (b): Preparation of (±)-2-benzamidocyclohexanone

A solution of Jones reagent (1135 ml) was prepared by combining $CrO_3$ (140 gm) and $H_2SO_4$ (122 ml) with Jones reagent was added dropwise to a cooled, stirred mixture of (±)-trans-2-benzamidocyclohexanol (260 gm) and acetone (3000 ml) and the stirring continued 1 hr. A 20% solution of $K_2CO_3$ in water was added to the reaction solution until the evolution of carbon dioxide subsided. The resulting layers were separated and the bottom layer extracted with ethyl acetate. The ethyl acetate was combined with the material from the upper layer and the resulting solution washed with water and saturated sodium chloride solution. The organic solution was concentrated on a rotary evaporator and the residue was recrystallized from aqueous 2-propanol to provide the product (mp 126°–127°C.).

Step (c): Preparation of (±)-cis-2-(1-pyrrolidinyl)-N-benzoylcyclohexylamine hydrochloride (±)-2-Benzamidocyclohexanone (213 gm) was combined with pyrrolidine (103 ml), p-toluenesulfonic acid (9.3 gm) and benzene (3300 ml) and heated to reflux for 23 hours. Additional pyrrolidine (103 ml) was added to the reaction mixture and the heating continued for 24 hours. The solvent was removed on a rotary evaporator to provide a crude enamine mixture. The crude material was dissolved in ethyl acetate (100 gm/200 ml) and hydrogenated over 10% Pd on carbon at 50 psi for 1.5 hours. The mixture was filtered through celite and the filtrate was concentrated on a rotary evaporator. The residue was combined with citric acid monohydrate (306 gm), water (1300 ml) and methylene chloride (500 ml) and shaken until all solid material had dissolved. The layers were separated and the aqueous layer was washed with additional methylene chloride. Excess concentrated aqueous ammonia was added to the aqueous solution and the mixture extracted with methylene chloride. The combined organic extracts were dried ($Na_2SO_4$) and the solvent removed on a rotary evaporator. The crude material was dissolved in methanol (200 ml) and treated with an excess of a solution of anhydrous hydrogen chloride in methanol. The solution was adjusted to a final volume of 700 ml by the addition of 2-propanol and the methanol was removed by distillation while maintaining a constant volume of 700 ml by the slow addition of 2-propanol. The crude product crystallized upon slow cooling and was filtered. The material was recrystallized from 2-propanol to provide the product (mp 276°–277°C.).

Step (d): Preparation of (±)-cis-2-(1-pyrrolidinyl) cyclohexylamine (±)-cis-2-(1-Pyrrolidinyl)-N-benzoylcyclohexylamine hydrochloride (10 gm) was combined with ethylene glycol (50 ml) and potassium hydroxide (10 gm) and the solution was heated to reflux for 48 hours. The solution was diluted with water (200 ml) and extracted with ether. The ether was removed on a rotary evaporator and the residue was distilled (94° C. at 0.05 mm Hg) to provide the product.

Step (e): Preparation of (−)-cis-2-(1-pyrrolidinyl) cyclohexylamine (±)-cis-2-(1-pyrrolidinyl)cyclohexylamine (10 gm) was combined with ethanol (10 ml) and 2-propanol (40 ml) and warmed to 60° C. A solution of R-(−)-mandelic acid (18 gm) in ethanol (50 ml) and 2-propanol (200 ml) was warmed to 60° C. and added to the amine solution. The solution was allowed to cool slowly to room temperature and the resulting crystals were filtered. The crystals were washed with 20% ethanol in 2-propanol, followed by ether and dried under vacuum. The crystals were recrystallized from 20% ethanol in 2-propanol to provide the mandelate salt. The salt was partitioned between 30% NaOH and chloroform and the layers separated. The chloroform was removed on a rotary evaporator to provide the product as a colorless oil which solidified upon standing (bp 86° C. at 0.1 mm Hg, $[a]_D$ (MeOH)=−2.95°).

Step (f): Preparation of (+)-cis-2-(1-pyrrolidinyl) cyclohexylamine

The mother liquors from Step (e) of Example 1 were concentrated on a rotary evaporator. The residue was partitioned between 30% NaOH and chloroform and the layers separated. The chloroform was removed on a rotary evaporator and the residue was distilled under high vacuum. The distillate was combined with ethanol (10 ml) and 2-propanol (40 ml) and warmed to 60° C. A solution of R-(−)-mandelic acid (18 gm) in ethanol (50 ml) and 2-propanol (200 ml) was warmed to 60° C. and added to the amine solution. The solution was allowed to cool slowly to room temperature and the resulting crystals were filtered. The crystals were washed with 20% ethanol in 2-propanol, followed by ether and dried under vacuum. The crystals were recrystallized from 20% ethanol in 2-propanol to provide the mandelate salt. The salt was partitioned between 30% NaOH and chloroform and the layers separated. The chloroform was removed on a rotary evaporator to provide the product as a colorless oil which solidified upon standing (bp 86° C. at 0.1 mm Hg, $[a]_D$ (MeOH)=+2.21°).

Step (g): Preparation of 1R, 2S-(−)-cis-2-(1-pyrrolidinyl)-N-methylcyclohexylamine (−)-cis-2-(1-pyrrolidinyl)cyclohexylamine (2 gm) was combined with ethyl formate (20 ml) and heated to reflux 10 minutes. The solvent was removed on a rotary evaporator. The residue was combined with anhydrous tetrahydrofuran (10 ml) and treated with 1M lithium aluminum hydride in tetrahydrofuran (16 ml). The mixture was heated to reflux 1 hour and cooled in an ice bath. The mixture was treated with water (2.4 ml) and 15% NaOH (0.6 ml), filtered, and the solvent removed on a rotary evaporator. The residue was distilled under high vacuum to provide the product as a colorless oil (bp 76° C. at 1.1 mm Hg, $[a]_D$ (MeOH)=−31.7°).

Step (h): Preparation of (±)-2-(N-t-butyloxycarbonyl-N-methylamino)cyclohexanone (±)-trans-N-methyl-2-aminocyclohexanol (142 gm) was combined with t-butyldicarbonate (240 gm), potassium bicarbonate (458 gm), and water (1000 ml) and stirred overnight. The aqueous mixture was extracted with methylene chloride and the organic extract was dried (Na$_2$SO$_4$) and concentrated on a rotary evaporator. The residue was recrystallized from isooctane to provide a white solid (mp 82°–83° C.). The solid was dissolved in methylene chloride (500 ml) and added dropwise to a stirred solution of pyridinium chlorochromate (334 gm) in methylene chloride (1000 ml). After the addition, stirring was continued for 3 hours. The mixture was diluted with ether (1500 ml) and filtered through florisil. The solvent was removed on a rotary evaporator and the residue was distilled (115° C. at 0.9 mm Hg) to provide a colorless oil.

Step (i): Preparation of (±)-cis-2-[1-pyrrolidinyl]-N-methylcyclohexylamine (±)-cis-2-Pyrrolidinyl-N-t-butyloxycarbonyl-N-methylcyclohexylamine (247 gm) was slowly added to 6M hydrochloric acid at 60° C. with vigorous stirring. The solution was stirred an additional 5 minutes at 60° C. and poured onto ice (200 gm). Excess concentrated aqueous ammonia was added and the mixture was extracted with methylene chloride. The combined extracts were dried (Na$_2$SO$_4$) and the solvent removed on a rotary evaporator. The residue was distilled (78° C. at 0.3 mm Hg) to give the product as a colorless oil.

Step (j): Preparation of (±)-cis-N-[2-(3,4-dichlorophenyl) ethyl]-N-methyl-2-(1-pyrrolidinyl)cyclohexylamine (Compound No. 1)

(±)-cis-2-Pyrrolidinyl-N-methylcyclohexylamine (3 gm) was combined with anhydrous dimethylformamide (70 ml) and warmed to 60° C. 2-(3,4-dichlorophenyl)ethyl methanesulfonate (14 gm) was added to the warm amine solution over 3 days. The reaction mixture was diluted to 500 ml with water and extracted with chloroform. The combined extracts were washed with water and treated with a solution of hydrogen bromide in methanol. The solution was concentrated on a rotary evaporator and the residual dimethylformamide removed by distillation under high vacuum. The residue was triturated with 2-propanol to provide a white solid. The solid was recrystallized from 2-propanol. Analytical data are reported in Table I.

EXAMPLE 2

Preparation of (±)-cis-N-[2-(3,4-dichlorophenyl) ethyl]-2-(1-pyrrolidinyl)-cyclohexylamine (±)-cis-2-(1-pyrrolidinyl)cyclohexylamine (5 gm) was combined with pyridine (1.2 gm), chloroform (200 ml), 3,4-dichlorophenylacetic acid (9.15 gm), and dicyclohexylcarbodiimide (12.3 gm) and the mixture was stirred for 12 hr at room temperature. The mixture was filtered, the precipitate was washed with ether (100 ml) and the filtrate and ether wash were combined. The organic solution was diluted with ether (200 ml) and extracted with 10% citric acid in water (300 ml). The acid layer was washed with ether (2×200 ml), then treated with excess concentrated aqueous ammonia until basic. The resulting mixture was extracted with methylene chloride (2×200 ml) and the combined organic extracts were washed with water (2×50 ml) and concentrated on a rotary evaporator. The resulting white solid was combined with tetrahydrofuran (25 ml) and added dropwise to a solution of AlH$_3$ in tetrahydrofuran (76.2 ml of a 0.665M solution) at room temperature. After the addition, the mixture was poured into 15% NaOH and the resulting mixture was extracted with ether (3×100 ml). The ether was removed on a rotary evaporator and the residue was dissolved in ethanol (100 ml). The ethanol was removed on a rotary evaporator and the residue was converted to the hydrogen bromide salt which was recrystallized from ethanol. Analytical data are reported in Table I.

The overall synthon for preparing compounds of Examples 3 to 6 is shown below, which is explained in more detail in the detailed description of Examples 3 to 6 which follows the synthon.

EXAMPLE 3

Preparation of 1R,2S-(−)-cis-N-[2-(3,4-dichlorophenyl)ethyl]-2-(1-pyrrolidinyl)cyclohexylamine Step (a): Preparation of 2-(1-pyrrolidinyl)cyclohexanone (b)

A solution of oxalyl chloride (50 mL, 0.5732 mol) in 200 mL of freshly distilled $CH_2Cl_2$ was cooled down to −70° C. and DMSO (80 mL, 1.1274 mol) was carefully added dropwise. After 15 min., 2-(1-pyrrolidinyl)cyclohexanol (a) (70 g, 0.4142 mol) was added to the reaction mixture, followed by $Et_3N$ (350 mL). The cold bath was then

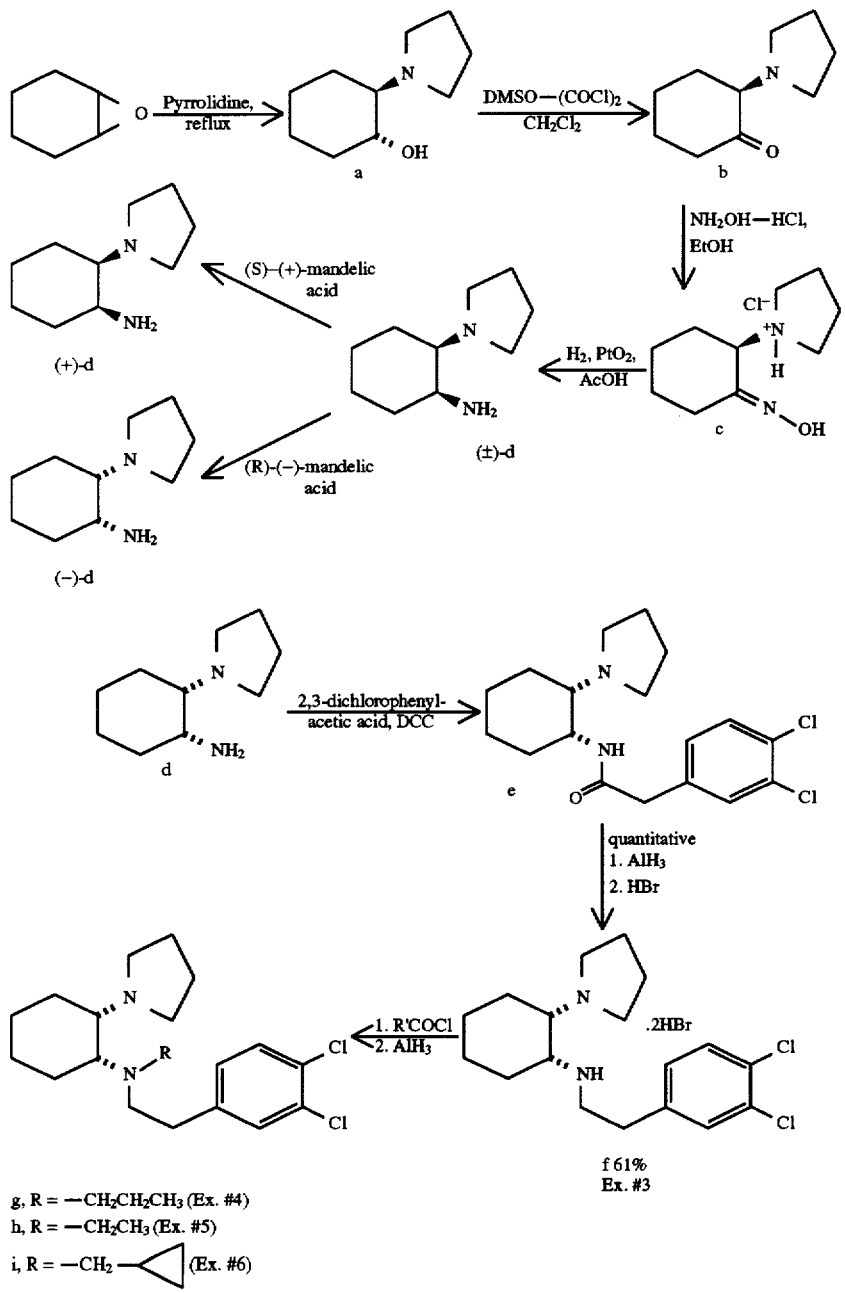

Synthon for Ex. #3 to Ex. #6 g, R = —CH₂CH₂CH₃ (Ex. #4)
h, R = —CH₂CH₃ (Ex. #5)
i, R = —CH₂—◁ (Ex. #6)

removed, and the mixture was stirred at room temperature for two and a half hours. Progress of the reaction was followed by gas chromatography. The solvent was partially removed in vacuo and ethyl ether (200 mL) was added. This organic layer was washed with brine (3×100 mL), dried (Na$_2$SO$_4$), and the solvent removed in vacuo. The crude product was distilled under high vacuum (BP: 84° C./0.5 mmHg) to yield 49.5 g of the ketone (b) as a colorless oil (72%). R$_f$: 0.49 (CHCl$_3$:MeOH:NH$_4$OH=92:7:1); B.P: 84° C. (0.5 mmHg); IR (neat) 2940, 2860, 2800, 1715, 1440 cm$^{-1}$; $^1$H-NMR (CDCl$_3$) d 1.53–1.63 (m, 1H), 1.72 (m, 4H), 1.76–1.93 (m, 4H), 1.94–2.04 (m, 1H), 2.21, (m, 1H), 2.52 (m, 5H), 2.83 (dd, 1H, J$_1$=8.6, J$_2$=4.5 Hz); Mass Spectrum Calcd. for C$_{10}$H$_{17}$NO: 167.1310, Found: 167.1310.

Step (b): Preparation of 2-(1-pyrrolidinyl)cyclohexanone oxime (c)

2-(1-Pyrrolidinyl)cyclohexanone (b) (46.15 g, 0.276 mol) was dissolved in EtOH (175 mL) and NH$_2$OH.HCl (23.4 g, 0.337 mol) was added. Reaction progress was followed by gas chromatography. The solvent was removed in vacuo, the residue was dissolved in MeOH, and the solution was poured into an Erlenmeyer flask. EtOAc was added to replace the MeOH while the mixture was boiling. In this way, crystallization of the hydrochloride of the oxime occurred, and 53.06 g of salt was obtained (88%). R$_f$: 0.44 (CHCl$_3$:MeOH:NH$_4$OH=90:9:1); M.P. (HCl salt): 170°–171° C.; IR (neat) 3400, 2960, 1640, 1450 cm$^{-1}$; $^1$H-NMR (CDCl$_3$) d 1.36–1.58 (m, 3H), 1.73 (m, 4H), 1.79–1.88 (m, 2H), 2.02–2.15 (m, 2H), 2.46–2.54 (m, 2H), 2.69 (m, 1H), 3.02 (bd, 1H, J=13.4 Hz), 8.35 (bs, 1H); Mass Spectrum (70 eV, m/e (rel. int.)) 182 (15, M$^+$), 166 (100), 148 (29), 136 (27), 124 (29), 110 (100), 97 (100), 70 (60). Elemental Analysis: Calcd. for C$_{10}$H$_{19}$ClN$_2$O: C: 54.92, H: 8.70, N: 12.81, Cl: 16.25. Found: C: 54.81, H: 8.71, N: 12.78, Cl: 16.30.

Step (c): Preparation of (±) cis-2-(1-pyrrolidinyl) cyclohexylamine ((±)-d)

2-(1-pyrrolidinyl)cyclohexanone oxime (c) (22.95 g, 0.105 mol) was dissolved in glacial acetic acid (120 mL). PtO$_2$ (1 g) was added and the mixture was hydrogenated at 45 psi for 96 hours. During this time, the catalyst was filtered and renewed every 24 hours. The reaction was followed by gas chromatography. The PtO$_2$ was removed by filtration of the reaction mixture through celite and excess concentrated HCl was added. The solvent was removed in vacuo at 40°–50° C. and the resulting hydrochloride salt was dissolved in 100 mL of water. This aqueous solution was carefully basified to 30% w/v with pellets of NaOH and extracted with CHCl$_3$ (5×50 mL). The organic layer was dried (Na$_2$SO$_4$), and the solvent was removed in vacuo. The crude amine was distilled under high vacuum to yield 13.7 g of (±)-(78%) as a colorless unstable oil. bp: 94° C./0.05 mmHg. Ir (film): 3380, 3300, 2940, 1590, 1440, 1125, 835 cm$^{-1}$. (±)-d.HCl crystallized slowly from 2-propanol as small conglomerates: mp 263°–265° C. $^1$H-NMR (free base) (CDCl$_3$): d 1.00–1.18 (m, 1H), 1.20–1.40 (m, 5H), 1.50–1.68 (m, 6H), 1.74 (t, J=3.5 Hz, 1H), 1.78 (t, J=3.5 Hz, 1H), 2.30–2.48 (m, 4H), 3.08 (br s, 2H). EIms (m/z, rel. int.): 168 (31, M$^+$), 110 (100), 97 (42), 84 (92), 70 (33). Anal. Calcd. for C$_{10}$H$_{22}$N$_2$Cl$_2$: C 49.79, H 9.19, N 11.62; Found: C 49.82, H 9.19, N 11.67.

Step (d): Preparation of (1R,2S)-(−)-cis-3,4-dichlorophenyl-N-[2-(1-pyrrolidinyl)-cyclohexyl]acetamide [(−)-e]

3,4-Dichlorophenylacetic acid (7.3 g, 0.357 mol) was dissolved in CH$_2$Cl$_2$ (50 mL) and dicyclohexylcarbodiimide (7.4 g, 0.0357 mol) was added. The mixture was stirred at room temperature for half an hour. (−)-cis-2-(1-Pyrrolidinyl) cyclohexylamine ((−)-d) (3.0 g, 0.0179 mol) and pyridine (0.7 mL) were then added. After 5 minutes, the dicyclohexyl urea was filtered off, and the solvent was concentrated in vacuo. The residue was diluted with Et$_2$O (200 mL), and the resulting organic layer extracted with 5% citric acid (4×50 mL). The aqueous layer was washed with Et$_2$O (4×50 mL), basified with concentrated NH$_4$OH and extracted with CH$_2$Cl$_2$ (3×80 mL). The organic layer was washed with brine (50 mL), dried (Na$_2$SO$_4$) and the solvent removed in vacuo. 6.30 g (99%) of crude crystalline product was obtained. The amide was recrystallized as its fumarate salt from EtOAc to yield 7.70 g (92%) of pure (−)-e.fumarate.hemihydrate. R$_f$: 0.27 (CHCl$_3$:MeOH:NH$_4$OH= 95:4.5:0.5); M.P. (free base): 110°–111° C.; M.P. (fumarate salt): 159°–160 ° C.; [a]$_D$ (fumarate salt) −12.7° (0.11, MeOH); $^1$H-NMR (CDCl$_3$) d 1.16–1.35 (m, 4H), 1.43 (m, 1H), 1.70 (m, 5H), 1.85 (m, 1H), 2.11 (m, 1H), 2.29 (bd, 1H, J=13.4 Hz), 2.41–2.49 (m, 4H), 3.51 (s, 2H), 4.01 (s, 1H), 6.28 (bs, 1H), 7.15 (dd, 1H, J$_1$=8.3, J$_2$=2.0 Hz), 7.39 (d, 1H, J=8.3 Hz), 7.41 (d, 11H, J=2.0 Hz); Mass Spectrum: CI (NH$_3$) 355 (M$^+$) ; Elemental Analysis: Calcd. for C$_{18}$H$_{24}$Cl$_2$N$_2$O (free base): C: 60.85, H: 6.76, N: 7.89, Cl: 20.00. Found: C: 60.75, H: 6.82, N: 7.84, Cl: 20.07. Elemental Analysis: Calcd. for C$_{22}$H$_{28}$Cl$_2$N$_2$O$_5$.½H$_2$O (fumarate salt): C: 55.00, H: 6.04, N: 5.83, Cl: 14.79. Found: C: 55.22, H: 6.06, N: 5.84, Cl: 14.86

Step (e): Preparation of (1R,2S)-(−)-cis-N-[2-(3,4-dichlorophenyl)ethyl]-2-(1-pyrrolidinyl)cyclohexylamine [(−)-f; Compound #3]

Aluminum Hydride solution in THF (0.67 mmol/mL) (80 mL, 0.0531 mol) [prepared by procedures described in a publication of B. R. de Costa et al, J. Med. Chem., 33, 3100–3110 (1990)] was stirred at room temperature under argon and (1R,2S)-(−)-cis-3,4-dichlorophenyl-N-[2-(1-pyrrolidinyl) cyclohexyl]acetamide [(−)-e] (3.77 g, 0.0106 mol) in THF (30 mL) was added slowly. After 5 minutes the mixture was poured into ice-cooled 15% NaOH solution (100 mL). An oily compound separated from this aqueous layer, which was extracted with Et$_2$O (3×100 mL). The organic layers were combined, washed with brine (2×50 mL), dried (Na$_2$SO$_4$) and the solvent removed in vacuo. A yellowish oil was obtained, which was purified by crystallization with HBr in EtOH to yield 3.24 g (61%) of (−)-f.HBr. R$_f$: 0.27 (CHCl$_3$:MeOH:NH$_4$OH=90:9:1); M.P. (HBr salt): 274°–275° C.; [a]$_D$−11° (0.32, MeOH); $^1$H-NMR (CDCl$_3$) d 1.11–1.28 (m, 4H), 1.45–1.77 (m, 8H), 1.81–1.95 (m, 2H), 2.28–2.44 (m, 4H), 2.58–2.69 (m, 1H), 2.71–2.80 (m, 3H), 2.89–2.97 (m, 1H), 7.07 (dd, 1H, J$_1$=8.2, J$_2$=2.0 Hz), 7.32 (d, 1H, J=8.2 Hz), 7.33 (d, 1H, J=2 Hz); Mass Spectrum: CI (NH$_3$) 341 (M$^+$); Elemental Analysis: Calcd. for C$_{18}$H$_{28}$Br$_2$Cl$_2$N$_2$ (HBr salt): C: 42.97, H: 5.61, N: 5.57, total halogen as Cl: 28.23, total halogen as Br: 63.56. Found: C: .43.06, H: 5.62, N: 5.55, total halogen as Cl: 28.13, total halogen as Br: 63.40. Calcd. for C$_{18}$H$_{26}$Cl$_2$N$_2$ (free base): C: 3.34, H: 7.62, N: 8.21, Cl: 20.82. Found: C: 63.24, H: 7.68, N: 8.16, Cl: 20.86.

EXAMPLE 4

Preparation of (1R,2S)-(−)-cis-N-[2-(3,4-dichlorophenyl)-ethyl]-N-(n-propyl)-2-(1-pyrrolidinyl)cyclohexylamine [(−)g; Compound #4]

(1R,2S)-(−)-cis-N-[2-(3,4-dichlorophenyl) ethyl]-2-(1-pyrrolidinyl)cyclohexylamine [(−)-f] (1.0 g, 0.00293 mol), prepared by procedures of Step (d) of Example 3, was dissolved in CHCl$_3$ (10 mL) and stirred in the presence of anhydrous K$_2$CO$_3$ (2.0 g, 0.0147 mol). Propionyl chloride (0.54 g, 0.00587 mol) was then added and reaction progress was followed by TLC. After completion of the reaction, the mixture was diluted with $CHCl_3$ (10 mL) and extracted with 10% NaOH (10×10 mL). The organic layer was dried and the solvent was removed in vacuo to give 1.1 g of crude product, which was not further purified. $R_f$: 0.51 ($CHCl_3$:MeOH:$NH_4OH$=90:9:1). The crude amide (0.2 g) was reduced following procedures of Step (e) of Example 3 to give 0.18 g of product, which contained 10% of diamine as an impurity. The entire mixture was acylated with $Ac_2O$ and then the desired diamine g was purified by crystallization with fumaric acid in EtO. $R_f$: 0.44 ($CHCl_3$:MeOH:$NH_4OH$=90:9:1); MP: 168°–169° C.; $[a]_D$– 11.1° (0.38, MeOH); Elemental Analysis: Calcd. for $C_{25}H_{36}Cl_2N_2O_4 \cdot H_2O$ (fumarate salt): C: 58.03, H: 7.35, N: 5.41. Found: C: 58.03, H: 7.06, N: 5.66.

EXAMPLE 5

Preparation of (1R,2S)-(–)-cis-N-ethyl-N-[2-(3,4-dichlorophenyl)ethyl]-2-(1-pyrrolidinyl)cyclohexylamine [(–)-h; Compound #5]

The title compound was prepared following the procedures of Example 4, except that $Ac_2O$ was used instead of propionyl chloride to obtain the amide. Diamine h was purified as the HI salt and recrystallized from MeOH. $R_f$: 0.42 ($CHCl_3$:MeOH:$NH_4OH$=90:9:1); MP: 215.5°–216.5° C.; $[a]_D$–8.2° (0.09, MeOH); Elemental Analysis: Calcd. for $C_{20}H_{32}Cl_2I_2N_2$ (HI salt): C: 38.40, H: 5.12, N: 4.48, Cl: 11.36. Found: C: 38.42, H: 5.24, N: 4.47, Cl: 11.24.

EXAMPLE 6

Preparation of (1R,2S)-(–)-cis-N-[2-(3,4-dichlorophenyl)ethyl]-N-cyclopropylmethyl-2-(1-pyrrolidinyl)cyclohexylamine [(–)-i; Compound #6]

The title compound (–)-i was prepared following the procedures of Example 4, purified as the fumarate salt and recrystallized from EtOAc. $R_f$: 0.47 ($CHCl_3$:MeOH:$NH_4OH$=90:9:1); MP: 183°–184° C.; $[a]_D$– 28.3° (0.30, MeOH); Elemental Analysis: Calcd. for $C_{26}H_{36}Cl_2N_2O_4$ (fumarate salt): C: 61.05, H: 7.09, N: 5.48. Found: C: 61.11, H: 7.13, N: 5.45.

Table I is a list of 17 specific compounds of most interest within Formula I. These compounds may be prepared by the methods described in the "General Synthetic Procedures" as well as by the more detailed methods contained in the specific preparations of Examples 1 to 6, above.

TABLE I

| Compound No. | Name | Structure | Elemental Theor. | Analysis Found | Melting Point | Specific Rotation $[α]_D$ | Mass Spectral Analysis |
|---|---|---|---|---|---|---|---|
| 1 | (±)-cis-N-[2-(3,4-dichlorophenyl)ethyl]-N-methyl-2-(1-pyrrolidinyl)cyclohexylamine | 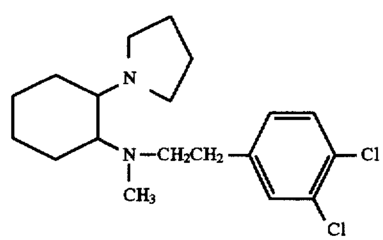 | C 56.63 H 6.79 N 6.29 | 56.43 6.91 6.33 | 120–125° C. oxalate salt | — | — |
| 2 | (±)-cis-N-[2-(3,4-dichlorophenyl)ethyl]-2-(1-pyrrolidinyl)-cyclohexylamine | 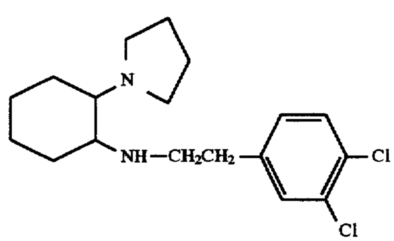 | C 42.96 H 5.57 N 5.57 | 43.04 5.65 5.54 | 274–275° C. HBr salt | — | — |
| 3 | 1R,2S-(-)-cis-N-[2-(3,4-dichlorophenyl)ethyl]-2-(1-pyrrolidinyl)cyclohexylamine | 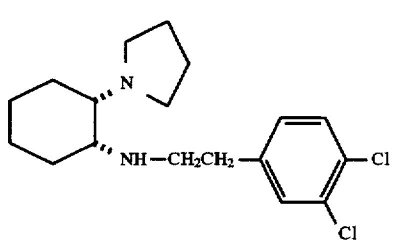 | C 42.96 H 5.57 N 5.57 | 43.03 5.61 5.57 | 274–275° C. HBr salt | –11.1° (0.32, MeOH) | — |

TABLE I-continued

| Compound No. | Name | Structure | Elemental Theor. | | Analysis Found | Melting Point | Specific Rotation $[\alpha]_D$ | Mass Spectral Analysis |
|---|---|---|---|---|---|---|---|---|
| 4 | 1R,2S-(-)-cis-N-[2-(3,4-dichlorophenyl)ethyl]-N-(n-propyl)-2-(1-pyrrolidinyl)cyclohexylamine | 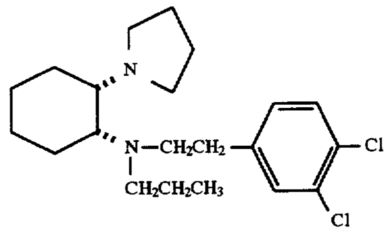 | C<br>H<br>N | 58.03<br>7.35<br>5.41 | 58.03<br>7.06<br>5.66 | 168–169° C.<br>fumarate salt | −11.1°<br>(0.38, MeOH) | — |
| 5 | 1R,2S-(-)-cis-N-[2-(3,4-dichlorophenyl)ethyl]-N-ethyl-2-(1-pyrrolidinyl)cyclohexylamine | 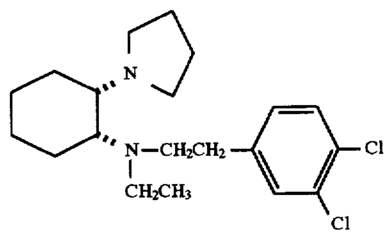 | C<br>H<br>N | 38.40<br>5.12<br>4.48 | 38.47<br>5.22<br>4.51 | 215.5–216.5° C.<br>HI salt | −8.2°<br>(0.09, MeOH) | — |
| 6 | 1R,2S-(-)-cis-N-[2-(3,4-dichlorophenyl)ethyl]-N-cyclopropylmethyl-2-(1-pyrrolidinyl)cyclohexylamine | 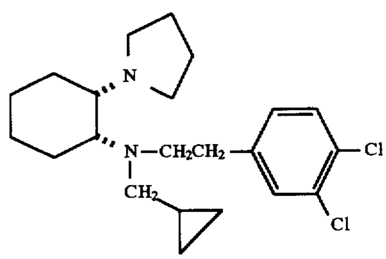 | C<br>H<br>N | 61.05<br>7.09<br>5.48 | 61.11<br>7.13<br>5.45 | 183–184° C.<br>fumarate salt | −28.3°<br>(0.30, MeOH) | — |
| 7 | 1S,2R-(-)-cis-N-[2-(3,4-dichlorophenyl)ethyl]-N-methyl-2-(1-pyrrolidinyl)cyclohexylamine | 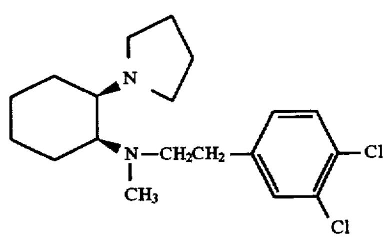 | C<br>H<br>N | 44.12<br>5.85<br>5.42 | 44.07<br>5.88<br>5.44 | 215–217° C.<br>HBr salt | −8.6°<br>(0.84, MeOH) | — |
| 8 | 1R,2S-(+)-cis-N-[2-(3,4-dichlorophenyl)ethyl]-N-methyl-2-(1-pyrrolidinyl)cyclohexylamine | 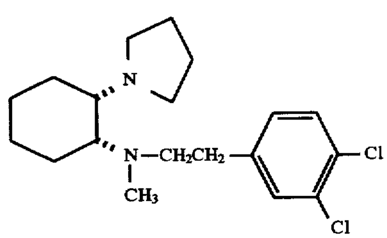 | C<br>H<br>N | 44.12<br>5.85<br>5.42 | 44.21<br>5.91<br>5.40 | 217–218° C.<br>HBr salt | +8.0°<br>(0.57, MeOH) | — |
| 9 | (±)-cis-N-methyl-N-[2-phenylethyl)-2-(1-pyrrolidinyl)cyclohexylamine | 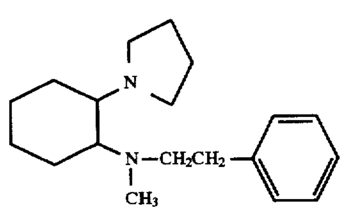 | — | | — | oil | | M+ (found) 286.242 Requires 286.241 |

TABLE I-continued

| Compound No. | Name | Structure | Elemental Theor. | Analysis Found | Melting Point | Specific Rotation $[\alpha]_D$ | Mass Spectral Analysis |
|---|---|---|---|---|---|---|---|
| 10 | (±)-cis-N-methyl-N-[2-(2-naphthyl)ethyl]-2-(1-pyrrolidinyl)cyclohexylamine | 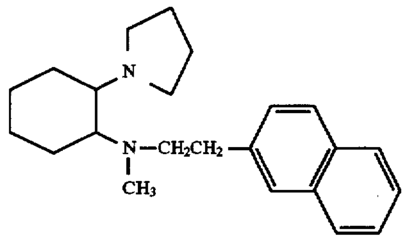 | — | — | oil | | M+ (found) 336.256 Requires 336.257 |
| 11 | 1S,2R-(-)-cis-N-methyl-N-[2-(3,4-methylenedioxyphenyl)ethyl]-2-(1-pyrrolidinyl)cyclohexylamine | 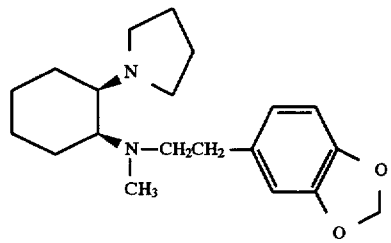 | C 48.79<br>H 6.55<br>N 5.69 | 48.68<br>6.59<br>5.68 | 248–249° C. HBr salt | −13.0 (3.99, H₂O) | — |
| 12 | 1R,2S-(+)-cis-N-methyl-N-[2-(3,4-methylenedioxyphenyl)ethyl]-2-(1-pyrrolidinyl)cyclohexylamine | 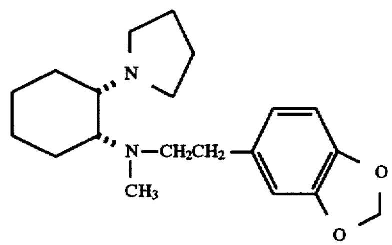 | C 48.79<br>H 6.55<br>N 5.69 | 48.64<br>6.60<br>5.62 | 248–249° C. HBr salt | +15.2° (2.16, H₂O) | — |
| 13 | 1S,2R-(+)-cis-N-[2-(3,4-dichlorophenyl)ethyl]-2-(1-pyrrolidinyl)cyclohexylamine | 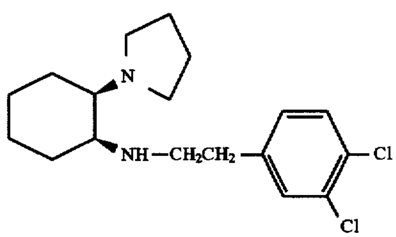 | C 42.96<br>H 5.57<br>N 5.57 | 43.03<br>5.62<br>5.59 | 274–275° C. HBr salt | +11.5° (0.57, MeOH) | — |
| 14 | 1S,2R-(+)-cis-N-[2-(3,4-dichlorophenyl)ethyl]-N-ethyl-2-1)cyclo- | 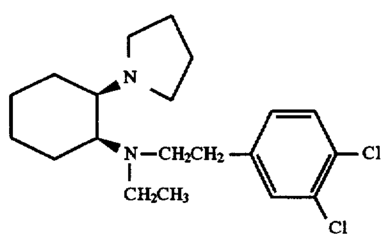 | C 38.47<br>H 5.22<br>N 4.51 | 38.50<br>5.15<br>4.43 | 215–215.5° C. HI salt | +7.8° (0.32, MeOH) | — |
| | N-[2-(3,4-)ethyl]-N-hyl-2 yl) e | | C 61.05<br>H 7.09<br>N 5.48 | 61.09<br>7.10<br>5.47 | 183–184° C. fumarate salt | +29.9° (0.35, MeOH) | — |

TABLE I-continued

| Compound No. | Name | Structure | Elemental Theor. | Analysis Found | Melting Point | Specific Rotation $[\alpha]_D$ | Mass Spectral Analysis |
|---|---|---|---|---|---|---|---|
| 16 | 1S,2R-(+)-cis-N-[2-(3,4-dichlorophenyl)ethyl]-N-(1-propyl)-2-(1-pyrrolidinyl)cyclohexylamine | 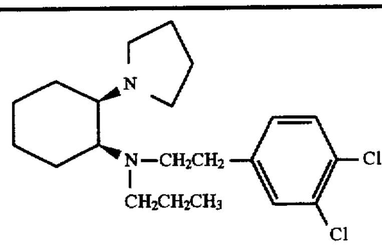 | C 60.12<br>H 7.26<br>N 5.61 | 6.03<br>7.26<br>5.52 | 168–169° C. fumarate salt | −15.0<br>(0.31, MeOH) | — |
| 17 | (±)-cis-N-[2-(3,4-dichlorophenyl)-methyl]-N-methyl-2-(1-pyrrolidinyl)cyclohexylamine | 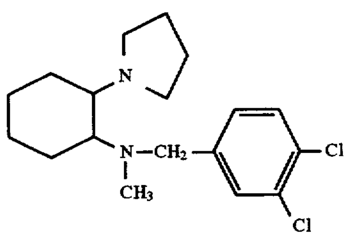 | C 42.97<br>H 5.61<br>N 5.57 | 43.12<br>5.78<br>5.20 | 215–217° C. HBr salt | −8.6°<br>(0.84, MeOH) | — |

Biological Evaluation

Radioreceptor Assay in Rat Brain Homogenate

Compounds #1, #7 and #8 were compared against di-o-tolylguanidine (DTG) [E. Weber et al, *Proc. Nat'l. Acad. Sci.*, 83, 8784–8788, 1986] to determine the relative potency of the compounds interacting with the sigma receptor. To determine the effects of the compounds in a sigma receptor assay, crude membrane preparations were prepared as follows. Brains from male Sprague-Dawley rats were homogenized in 10 volumes (wt/vol) of 0.32M sucrose, using a Polytron grinder. The homogenate was centrifuged at 900×G for 10 minutes at 4° C. The supernatant was collected and centrifuged at 22,000×g for 20 minutes at 4° C. The pellet was resuspended in 10 volumes of 50 mM Tris/HCl buffer (pH 7.4) and centrifuged at 22,000×g for 20 minutes at 4° C. The pellet was resuspended in 5 mM Tris/HCl buffer (pH 7.4) to give a final concentration of 250 mg/ml of the crude material. Incubation tubes were prepared in triplicate and contained 0.1 ml of tissue suspension, 2 nM of [$^3$H]-(+)-1-propyl-3-(3-hydroxyphenyl)piperidine {[$^3$H]-3-(+)-PPP}, and varying concentrations of the displacing ligand (0.1–1000 nM) in a final volume of 0.5 ml. After a 1 hr incubation at room temperature, the contents of the test tubes were filtered through GS filter paper which had been pre-soaked for at least 2 hours in 0.05% polyethyleneamine. The test tubes were rinsed three times with Tris/HCl buffer. Radioactivity on the filters was determined and $IC_{50}$ values were calculated from inhibition curves using the method of Cheng and Prusoff [*Biochem. Pharmacol.*, 22, 3099–3108, 1973]. Results are shown in Table II.

TABLE II

| Test Compound | Ki apparent (nM)<br>(units ± SEM) |
|---|---|
| DTG | 47 ± 5 |
| Compound No. 1 | 230 ± 70 |
| Compound No. 7 | 30 ± 10 |
| Compound No. 8 | 20 ± 1 |

Radioreceptor Assay in Guinea Pig Brain Homogenate

Receptor binding assays were performed using the crude synaptosomal ($P_2$) membrane fraction of guinea pig brain for sigma receptors. Crude $P_2$ membrane fractions were prepared from frozen (−80° C.) guinea pig brains (Pel-Freeze, Rogers, Ak.), minus cerebellum. After removal of cerebella, brains were allowed to thaw slowly on ice and placed on ice-cold 10 mM Tris-HCl, pH 7.4 containing 320 mM sucrose (Tris-sucrose buffer). Brains were then homogenized in a Potter-Elvehjem homogenizer by 10 strokes of a motor driven Teflon pestle in a volume of 10 mL/gm tissue wet weight. The homogenate was centrifuged at 1,000×g for 10 min. at 4° C. and the supernatants saved. The pellets were re-suspended by vortexing in 2 ml/g ice-cold TRIS-sucrose and centrifuged again at 1000×g for 10 minutes. The combined 1000×g supernatants were centrifuged at 31,000×g for 15 minutes at 4° C. The pellets were resuspended by vortexing in 3 mL/gm of 10 mM Tris-HCl, pH 7.4 and the suspension allowed to incubate at 25° C. for 15 min. Following centrifugation at 31,000×g for 15 min., the pellets were resuspended by gentle Potter-Elvehjem homogenization to a final volume of 1.53 mL/gm in 10 mM Tris-HCl pH 7.4. Aliquots were stored at −80° C. until use. Protein concentration was determined by the method of Lowry et al using bovine serum albumen as standard. The sigma receptors were labelled with [$^3$H]-(+)-3-PPP (98.9 Ci/mmol). Incubations were carried out in 50 mM TRIS-HCl, pH 8.0, for 120 min. at 25° C. in a volume of 0.5 mL with 500 µg of membrane protein and 3 nM [$^3$H]-(±)-3-PPP. Nonspecific binding was determined in the presence of 1 µM haloperidol. Assays were terminated by the addition of 5 mL of ice-cold 10 mM TRIS-HCl, pH 8.0, and filtration through glass fir filters (Schleicher and Schuell), which were soaked in 0.5% poly(ethyleneimine) for at least 30 min. at 25° C. prior to use. Filters were then washed twice with 5 mL of ice-cold TRIS-HCl buffer. In order to obtain an initial estimate of the binding affinity of the compounds, each compound was initially tested at 3 concentrations in the sigma assay (100, 1000, 10000 nM). If a compound elicited greater than 30% inhibition of binding of the test ligand ($[^3H]$-(+)-3-PPP) at 10000 nM, a twelve point curve using unlabeled test ligand concentrations ranging from 0.05–10000 nM (0.005–1000 nM for the most potent compounds) was conducted. The CDATA (EMF Software, Inc., Baltimore, Md.) iterative curve fitting program was used to analyze the results. These results were obtained from two, or in some cases three, experiments (± SEM), each carried out in duplicate. Results are shown in Table III.

TABLE III

| Test Compound No. | $K_i$ (nM) (units ± SEM) |
|---|---|
| 1 | 1.8 ± 0.4 |
| 2 | NT |
| 3 | 0.49 ± 0.04 |
| 4 | 56 ± 9.9 |
| 5 | 3.5 ± 1.0 |
| 6 | 38 ± 13 |
| 7 | 1.3 ± 0.3 |
| 8 | 6.0 ± 3 |
| 9 | 113 ± 8 |
| 10 | 33 ± 5 |
| 11 | 90 ± 20 |
| 12 | 31 ± 0.05 |
| 13 | 2.4 ± 0.8 |
| 14 | 3.1 ± 0.55 |
| 15 | 412 ± 69 |
| 16 | 140 ± 17 |
| 17 | 1.2 ± 0.03 |

NT = Not Tested

Blockage of Apomorphine-induced Climbing

Compounds of the invention were evaluated for their ability to block apomorphine-induced climbing. The evaluation of the compounds followed the method outlined by Protais [*Psychopharmcol.*, 50, 1–6, 1976]. Swiss-Webster mice, weighing 20–25 g, are pretreated with the compounds of the invention by i.p. or s.c. administration at various times before 2 mg/kg apomorphine is administered s.c. in a volume of 1 ml/kg. All test compounds are administered in a volume of 10 ml/kg. Mice are rated at 10 and 20 minutes after apomorphine administration using the following rating scale: (0) forepaws on the floor, (1) forefeet holding the bars, and (2) four paws holding bars. Dose-response curves are analyzed by a computerized Finney assay [*Statistical Methods in Biological Assays*, 2nd Edn., Hatner Pub. Co., New York (1964)]. Compound No. 8 completely blocked apomorphine-induced climbing at a dose of 10 mg/kg.

Forebrain ischemia Assay

Male Mongolian gerbils, 50–70 gm, were used as subjects. Compound No. 8 (50 mg/kg) was injected i.p. 30 minutes prior to carotid occlusion into 6 gerbils. In preparation for surgical procedures, the animals were lightly anesthetized with halothane and placed upside down on a heated pad with their snout within a nosecone. Nitrous oxide (70%): oxygen (30%) plus 0.5% halothane was circulated through the nosecone to provide continuous anesthesia throughout the surgical procedure. A midline incision was made in the neck and the carotid arteries were exposed. A length of suture thread was placed under each carotid. The thread was then tightened around each carotid and pressure applied to the thread to insure flow as occluded. Flow was occluded for 15 minutes and then the thread was removed. The carotids were visually inspected to confirm that reflow had occurred. The wound was then closed with autoclips and the gerbils allowed to recover. Following surgery, the gerbils were kept alive for 7 days. They were anesthetized with 100 mg/kg sodium pentobarbital and perfused transcardially with saline (with heparin) followed by buffered formalin. The brain was removed, trimmed and prepared for histological processing. Sections (10 microns) were stained with thionin. At 7 days following the ischemic insult, damaged neurons have been cleared away by glia and the extent of damage can be ascertained within the vulnerable CA1 region of the hippocampus. The degree of lesion in the CA1 region of the hippocampus was quantified by counting the pyramidal cell bodies in a 0.5 mm length of CA1 on the section corresponding to P 1.7 mm in the atlas of Loskota, Lnax and Verity [W. J. Loskota et al, *A Stereotaxic Atlas of the Mongolian Gerbil Brain*, Ann Arbor Science Publishers, Ann Arber, p. 77 (1974)]. The cell loss was significantly reduced in the gerbils given Compound No. 8 ($p<0.01$).

Circling Behavior Assay

In order to assess the utility of compounds of the invention in treatment of Parkinsonism, the ability of the compound to stimulate movement following microinjections in the substantia nigra was assessed. Parkinson's disease results from the degeneration of dopamine-secreting neurons in the substantia nigra resulting in a reduced ability to generate movement. Compound #1 binds to sigma receptors, which are highly concentrated in the substantia nigra. The demonstration of increased motor activity, following compound administration in this part of the brain, would therefore suggest a stimulatory action on the substantia nigra. Such a stimulatory action would predict increased ability to generate voluntary movement in Parkinson's patients showing decreased functionality of this brain area. Current treatments of Parkinson's disease also stimulate this brain area, but show significant side effects that may not be present in compounds of the invention. The following experiments demonstrate the ability of compounds of the invention to stimulate motor activity following microinjections in the substantia nigra. It is expected, therefore, that compounds of the invention would have clinical utility in the treatment of Parkinson's disease and other disorders in which there is a paucity of movement.

Three to seven days before behavioral testing, each animal (245–350 g, N=57) was anesthetized with 50 mg/kg sodium pentobarbital and mounted in a Narishige stereotaxic apparatus. A guide cannula, constructed from 24 gauge thinwall stainless steel tubing, was implanted with its tip 4.0 mm above the left substantia nigra pars reticulata (coordinates: 3.2 mm anterior; 2.2 mm lateral; 4.7 mm ventral), from lambda and the skull surface. Cannulae were secured with stainless steel screws and dental acrylic. Stainless steel stylers kept the cannulae sealed except during drug infusion. All drugs were prepared on the day of testing. Animals were gently restrained and the drugs were administered in a volume of 0.5 ul over 72 seconds through a 31 gauge microneedle that was constructed to extend 4.0 mm beyond the tips of the guide cannulae. Dose studies of circling induced by Compound #1 followed the methods previously published for DTG. Animals received a single injection of saline (n=6), 1.5 nmol (n=5), 3.7 nmol (n=6), 9.3 nmol (n=7 or 14.9 nmol (n=5) in 0.5 ul 0.9% NaCl. Following injection, each animal was fitted with a harness which was connected to an optical position transducer interfaced to a computer that derived the number and direction of half turns for 30 min. Each rat received a single injection of the test drug to minimize tissue damage. Rats were sacrificed by an overdose of sodium pentobarbital and perfused intracardially with 10% formalin. Brains were fixed in a 30% sucrose-formalin solution and coronal sections (40 um) were taken throughout the extent of the injection site. The sections were stained with cresyl violet and examined under a microscope to localize injection sites. Only subjects with histologically confirmed injection sites were used in the data analyses. For the studies of circling behavior, the number of net (contalateral-isolateral) rotations were computed for each rat and subjected to analysis of variance. Repeated measures analysis of variance revealed that Compound #1 produced significant dose-related increases in circling behavior compared to the saline control following microinjectons in the substantia nigra ($F_{4,27}=3.09$; $p=0.032$). Consistent with the increased affinity of Compound #1 for sigma receptors, this effect occurred at doses lower than those necessary to produce the effect with (+)-pentazocine published previously. Results showing contralateral circling behavior produced by intranigral microinjections of various doses of Compound #1 are reported in Table IV and illustrated in FIG. 1.

Table IV shows the effect of Compound #1 and control (saline) on locomotor activity (½ contralateral rotations net in 30 min.) following microinjections in the substantia nigra. Individual subjects are shown along with the average and standard deviation of the effect. As illustrated, increasing doses of Compound #1 produce marked effects, which are statistically significant, as described above.

TABLE IV

Effect of Compound #1 on Locomotor Activity

| Drug Treatment | Rat Number | Net Turns | Stats |
|---|---|---|---|
| Saline | 57.00 | 1.00 | Average = 3.50 |
|  | 58.00 | 4.00 | Stan Dev = 4.35 |
|  | 59.00 | 12.00 |  |
|  | 62.00 | 0.00 |  |
|  | 63.00 | 5.00 |  |
|  | 64.00 | 1.00 |  |
| Compound #1 | 35.00 | 25.00 | Average = 11.00 |
| DOSE = 1.49 nmol | 38.09 | 17.00 | Stan Dev 18.94 |
|  | 40.00 | 5.00 |  |
|  | 50.00 | 4.00 |  |
|  | 66.00 | 38.00 |  |
| Compound #1 | 10.00 | 13.00 | Average = 18.33 |
| DOSE = 3.72 nmol | 11.00 | 23.00 | Stan Dev = 7.87 |
|  | 13.00 | 5.00 |  |
|  | 15.00 | 28.00 |  |
|  | 45.00 | 25.00 |  |
|  | 46.00 | 16.00 |  |
| Compound #1 | 1.00 | 28.00 | Average = 38.14 |
| DOSE = 9.3 nmol | 2.00 | 20.00 | Stan Dev 21.46 |
|  | 3.00 | 46.00 |  |
|  | 4.00 | 87.00 |  |
|  | 7.00 | 30.00 |  |
|  | 51.00 | 22.00 |  |
|  | 52.00 | 34.00 |  |
| Compound #1 | 24.00 | 6.00 | Average = 31.00 |
| DOSE = 14.9 nmol | 25.00 | 58.00 | Stan Dev = 27.08 |
|  | 26.00 | 13.00 |  |
|  | 27.00 | 61.00 |  |
|  | 29.00 | 7.00 |  |
|  | 30.00 | 75.00 |  |
|  | 32.00 | 24.00 |  |
|  | 34.00 | 4.00 |  |

Also embraced within this invention is a class of pharmaceutical compositions comprising one or more compounds of Formula I in association with one or more non-toxic, pharmaceutically-acceptable carriers and/or diluents and/or adjuvants (collectively referred to herein as "carrier" materials) and, if desired, other active ingredients. The compounds of the present invention may be administered by any suitable route, preferably in the form a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art. The compounds and composition may, for example, be administered intravascularly, intraperitoneally, subcutaneously, intramuscularly or topically.

For oral administration, the pharmaceutical compositions may be in the form of, for example, a tablet, capsule, suspension or liquid. The pharmaceutical composition is preferably made in the form of a dosage unit containing a particular amount of the active ingredient. Examples of such dosage units are tablets or capsules. These may with advantage contain an amount of active ingredient from about 1 to 250 mg, preferably from about 25 to 150 mg. A suitable daily dose for a mammal may vary widely depending on the condition of the patient and other factors. However, a dose of from about 0.1 to 3000 mg/kg body weight, particularly from about 1 to 100 mg/kg body weight, may be appropriate.

The active ingredient may also be administered by injection as a composition wherein, for example, saline, dextrose or water may be used as a suitable carrier. A suitable daily dose is from about 0.1 to 100 mg/kg body weight injected per day in multiple doses depending on the disease being treated. A preferred daily dose would be from about 1 to 30 mg/kg body weight. Compounds indicated for prophylactic therapy will preferably be administered in a daily dose generally in a range from about 0.1 mg to about 100 mg per kilogram of body weight per day. A more preferred dosage will be a range from about 1 mg to about 100 mg per kilogram of body weight. Most preferred is a dosage in a range from about 1 to about 50 mg per kilogram of body weight per day. A suitable dose can be administered, in multiple sub-doses per day. These sub-doses may be administered in unit dosage forms. Typically, a dose or sub-dose may contain from about 1 mg to about 100 mg of active compound per unit dosage form. A more preferred dosage will contain from about 2 mg to about 50 mg of active compound per unit dosage form. Most preferred is a dosage form containing from about 3 mg to about 25 mg of active compound per unit dose.

The dosage regimen for treating a disease condition with the compounds and/or compositions of this invention is selected in accordance with a variety of factors, including the type, age, weight, sex and medical condition of the patient, the severity of the disease, the route of administration, and the particular compound employed, and thus may vary widely.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely own in the pharmaceutical art.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A compound of the formula:

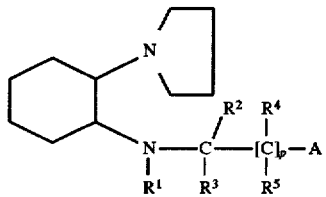

wherein:

p is an integer from 0 to 5;

$R^1$ is selected from the group consisting of hydrogen, $C_1$–$C_5$ alkyl, $C_3$–$C_8$ cycloalkyl or $C_4$–$C_8$ cycloalkylalkyl with the proviso that when $R^1$ is methyl, than p is not 1;

$R^2$, $R^3$, $R^4$ and $R^5$ are hydrogen; and

A is phenyl and wherein A may be further substituted with one or more halo substituents;

or a pharmaceutically acceptable salt thereof.

2. The compound according to claim 1, wherein:

p is an integer from 0 to 2;

$R^1$ is selected from the group consisting of hydrogen, methyl, ethyl, propyl and cyclopropylmethyl with the proviso that when $R^1$ is methyl, p is not 1;

$R^2$, $R^3$, $R^4$ and $R^5$ are hydrogen; and

A is phenyl and wherein A may be further substituted with one or more chlorine substituents;

or a pharmaceutically acceptable salt thereof.

3. The compound according to claim 2, wherein the compound is selected from the group consisting of:

(±)-cis-N-[2-(3,4-dichlorophenyl)ethyl]-2-(1-pyrrolidinyl)-cyclohexylamine;

1S,2R-(+)-cis-N-[2-(3,4-dichlorophenyl)ethyl]-2-(1-pyrrolidinyl)-cyclohexylamine;

1R,2S-(−)-cis-N-[2-(3,4-dichlorophenyl)ethyl]-2-(1-pyrrolidinyl)-cyclohexylamine;

1S,2R-(+)-cis-N-[2-(3,4-dichlorophenyl)ethyl]-N-ethyl-2-(1-pyrrolidinyl)cyclohexylamine;

1R,2S(−)-cis-N-[2-(3,4-dichlorophenyl) ethyl]N-ethyl-2-(1-pyrrolidinyl)cyclohexylamine;

1S,2R(+)-cis-N-[2-(3,4-dichlorophenyl)ethyl]-N-(1-propyl)-2-(1-pyrrolidinyl)cyclohexylamine;

1R,2S-(−)-cis-N-[2-(3,4-dichlorophenyl)ethyl]-N-(1-propyl)-2-(1-pyrrolidinyl)cyclohexylamine;

1S,2R-(+)-cis-N-[2-(3,4,-dichlorophenyl)ethyl]-N-cyclopropylmethyl-1-(1-pyrrolidinyl)cyclohexylamine;

1R,2S-(−)-cis-N-[2-(3,4-dichlorophenyl)ethyl]-N-cyclopropylmethyl-2-(1-pyrrolidinyl)-cyclohexylamine; or (±)-cis-N-[2-(3,4-dichlorophenyl)methyl]-N-methyl-2-(1-pyrrolidinyl)cyclohexylamine;

or pharmaceutically acceptable salts thereof.

4. A pharmaceutical composition comprising a therapeutically-effective amount of an active compound for treating or preventing a CNS-related disorder and a pharmaceutically-acceptable carrier or diluent, said active compound selected from the group consisting of:

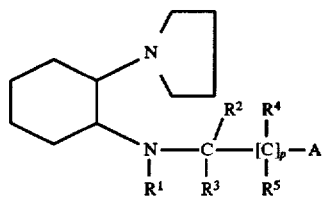

wherein:

p is an integer from 0 to 5;

$R^1$ is selected from the group consisting of hydrogen, $C_1$–$C_5$ alkyl, $C_3$–$C_8$ cycloalkyl or $C_4$–$C_8$ cycloalkylalkyl with the proviso that when $R^1$ is methyl, than p is not 1;

$R^2$, $R^3$, $R^4$ and $R^5$ are hydrogen; and

A is phenyl; wherein A may be further substituted with one or more halo substituents;

or a pharmaceutically acceptable salt thereof.

5. The composition of claim 4 wherein said active compound is selected from the group consisting of:

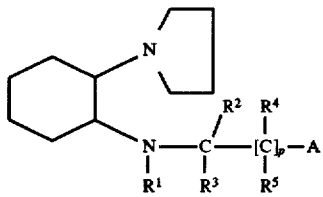

wherein p is an integer from 0 to 2;

$R^1$ is selected from the group consisting of hydrogen, methyl, ethyl, propyl and cyclopropylmethyl with the proviso that when $R^1$ is methyl, p is not 1;

$R^2$, $R^3$, $R^4$ and $R^5$ are hydrogen; and

A is phenyl and wherein A may be further substituted with one or more chlorine substituents;

or a pharmaceutically acceptable salt thereof.

6. The composition according to claim 5, wherein the compound is selected from the group consisting of:

(±)-cis-N-[2-(3,4-dichlorophenyl)ethyl]-2-(1-pyrrolidinyl)-cyclohexylamine;

1S,2R-(+)-cis-N-[2-(3,4-dichlorophenyl)ethyl]-2-(1-pyrrolidinyl)-cyclohexylamine;

1R,2S-(−)-cis-N-[2-(3,4-dichlorophenyl)ethyl]-2-(1-pyrrolidinyl)-cyclohexylamine;

1S,2R-(+)-cis-N-[2-(3,4-dichlorophenyl)ethyl]-N-ethyl-2-(1-pyrrolidinyl)cyclohexylamine;

1S,2R-(+)-cis-N-[2-(3,4-dichlorophenyl)ethyl]-N-ethyl-2-(1-pyrrolidinyl)cyclohexylamine;

1R,2S(−)-cis-N-[2-(3,4-dichlorophenyl)ethyl]-N-(1-propyl)-2-(1-pyrrolidinyl)cyclohexylamine;

1R,2S-(−)-cis-N-[2-(3,4-dichlorophenyl)ethyl]-N-(1-propyl)-2-(1-pyrrolidinyl)cyclohexylamine;
1S,2R-(+)-cis-N-[2-(3,4,-dichlorophenyl)ethyl]-N-cyclopropylmethyl-1-(1-pyrrolidinyl)cyclohexylamine;
1R,2S-(−)-cis-N-[2-(3,4-dichlorophenyl)ethyl]-N-cyclopropylmethyl-2-(1-pyrrolidinyl)-cyclohexylamine; or
(±)-cis-N-[2-(3,4-dichlorophenyl)methyl]-N-methyl-2-(1-pyrrolidinyl)cyclohexylamine;
or pharmaceutically acceptable salts thereof.

7. Method for treating a patient afflicted with or susceptible to a CNS-related disorder, which method comprises administering to said patient a therapeutically effective amount of a pharmaceutical composition containing a pharmaceutically-acceptable carrier or diluent, and an active compound selected from the group consisting of:

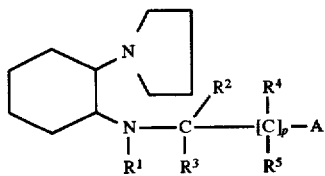

wherein:
p is an integer from 0 to 5;
$R^1$ is selected from the group consisting of hydrogen, $C_1$–$C_5$ alkyl, $C_3$–$C_8$ cycloalkyl or $C_4$–$C_8$ cycloalkylalkyl with the proviso that when $R^1$ is methyl, than p is not 1;
$R^2$, $R^3$, $R^4$ and $R^5$ are hydrogen; and
A is phenyl; wherein A may be further substituted with one or more halo substituents;
or a pharmaceutically acceptable salt thereof.

8. The method of claim 7 wherein the compound is selected from the group consisting of:

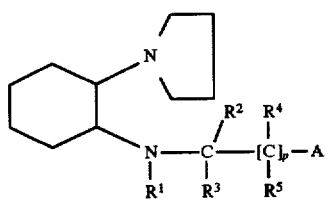

wherein
p is an integer from 0 to 2;
$R^1$ is selected from the group consisting of hydrogen, methyl, ethyl, propyl and cyclopropylmethyl with the proviso that when $R^1$ is methyl, p is not 1;
$R^2$, $R^3$, $R^4$ and $R^5$ are hydrogen; and A is phenyl and wherein A may be further substituted with one or more chlorine substituents;
or a pharmaceutically acceptable salt thereof.

9. The method of claim 8 wherein the compound is selected from the group consisting of:

(±)-cis-N-[2-(3,4-dichlorophenyl)ethyl]-2-(1-pyrrolidinyl)-cyclohexylamine;
1S,2R-(+)-cis-N-[2-(3,4-dichlorophenyl)ethyl]-2-(1-pyrrolidinyl)-cyclohexylamine;
1R,2S-(−)-cis-N-[2-(3,4-dichlorophenyl)ethyl]-2-(1-pyrrolidinyl)-cyclohexylamine;
1S,2R-(+)-cis-N-[2-(3,4-dichlorophenyl)ethyl]-N-ethyl-2-(1-pyrrolidinyl)cyclohexylamine;
1R,2S-(−)-cis-N-[2-(3,4-dichlorophenyl)ethyl]-N-ethyl-2-(1-pyrrolidinyl)cyclohexylamine;
1S,2R(+)-cis-N-[2-(3,4-dichlorophenyl)ethyl]-N-(1-propyl)-2-(1-pyrrolidinyl)cyclohexylamine;
1R,2S-(−)-cis-N-[2-(3,4-dichlorophenyl)ethyl]-N-(1-propyl)-2-(1-pyrrolidinyl)cyclohexylamine;
1S,2R-(+)-cis-N-[2-(3,4,-dichlorophenyl)ethyl]-N-cyclopropylmethyl-1-(1-pyrrolidinyl)cyclohexylamine;
1R,2S-(−)-cis-N-[2-(3,4-dichlorophenyl)ethyl]-N-cyclopropylmethyl-2-(1-pyrrolidinyl)-cyclohexylamine; or
(±)-cis-N-[2-(3,4-dichlorophenyl)methyl]-N-methyl-2-(1-pyrrolidinyl)cyclohexylamine;
or pharmaceutically acceptable salts thereof.

10. The method of claim 7 wherein said CNS-related disorder is cerebral ischemia.

11. The method of claim 7 wherein said CNS-related disorder is a psychotic disorder.

12. The method of claim 7 wherein said CNS-related disorder is a convulsive disorder.

13. (±)-cis-N-methyl-N-(2-phenylethyl)-2-(1-pyrrolidinyl)cyclohexylamine or a pharmaceutically acceptable salt thereof.

14. A pharmaceutical composition comprising a therapeutically-effective amount of (±)-cis-N-methyl-N-(2-phenylethyl)-2-(1-pyrrolidinyl)-cyclohexylamine or a pharmaceutically acceptable salt thereof for treating or preventing a CNS-related disorder and a pharmaceutically-acceptable carrier or diluent.

15. Method for treating a patient afflicted with or susceptible to a CNS-related disorder, which method comprises administering to said patient a therapeutically-effective amount of a pharmaceutical composition containing a pharmaceutically-acceptable carrier or diluent and (±)-cis-N-methyl-N-(2-phenylethyl)-2-(1-pyrrolidinyl)-cyclohexylamine or a pharmaceutically acceptable salt thereof.

* * * * *